US009801855B2

(12) United States Patent
Bansal et al.

(10) Patent No.: US 9,801,855 B2
(45) Date of Patent: Oct. 31, 2017

(54) NANOCRYSTALLINE SOLID DISPERSION COMPOSITIONS AND PROCESS OF PREPARATION THEREOF

(71) Applicant: NATIONAL INSTITUTE OF PHARMACEUTICAL EDUCATION AND RESEARCH (NIPER), Punjab (IN)

(72) Inventors: Arvind Kumar Bansal, Punjab (IN); Ajay Kumar Raju Dantuluri, Punjab (IN); Shete Ganesh Bhaskarao, Punjab (IN); Pawar Yogesh Bapurao, Punjab (IN)

(73) Assignee: NATIONAL INSTITUTE OF PHARMACEUTICAL EDUCATION AND RESEARCH (NIPER), Punjab (IN)

( * ) Notice: Subject to any disclaimer, the term of this patent is extended or adjusted under 35 U.S.C. 154(b) by 0 days.

(21) Appl. No.: 14/383,888

(22) PCT Filed: Mar. 7, 2013

(86) PCT No.: PCT/IB2013/051807
§ 371 (c)(1),
(2) Date: Sep. 8, 2014

(87) PCT Pub. No.: WO2013/132457
PCT Pub. Date: Sep. 12, 2013

(65) Prior Publication Data
US 2015/0132385 A1     May 14, 2015

(30) Foreign Application Priority Data

Mar. 7, 2012 (IN) .......................... 0674/DEL/2012

(51) Int. Cl.
| | |
|---|---|
| A61K 9/16 | (2006.01) |
| A61K 31/353 | (2006.01) |
| A61K 31/405 | (2006.01) |
| A61K 31/12 | (2006.01) |
| A61K 31/216 | (2006.01) |
| A61K 31/192 | (2006.01) |
| A61K 31/415 | (2006.01) |
| A61K 31/198 | (2006.01) |
| A61K 31/4184 | (2006.01) |
| A61K 31/496 | (2006.01) |
| A61K 31/635 | (2006.01) |
| A23D 7/005 | (2006.01) |
| A61K 31/197 | (2006.01) |
| A23P 10/30 | (2016.01) |
| A23L 33/10 | (2016.01) |
| A23L 33/105 | (2016.01) |
| A23L 33/12 | (2016.01) |
| A23L 33/15 | (2016.01) |

(Continued)

(52) U.S. Cl.
CPC .......... *A61K 31/415* (2013.01); *A23D 7/0053* (2013.01); *A23L 33/10* (2016.08); *A23L 33/105* (2016.08); *A23L 33/12* (2016.08); *A23L 33/15* (2016.08); *A23L 33/155* (2016.08); *A23L 33/16* (2016.08); *A23P 10/30* (2016.08); *A61K 9/1611* (2013.01); *A61K 9/1617* (2013.01); *A61K 9/1623* (2013.01); *A61K 31/12* (2013.01); *A61K 31/192* (2013.01); *A61K 31/197* (2013.01); *A61K 31/198* (2013.01); *A61K 31/216* (2013.01); *A61K 31/353* (2013.01); *A61K 31/405* (2013.01); *A61K 31/4184* (2013.01); *A61K 31/496* (2013.01); *A61K 31/635* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2003/0175313 A1* | 9/2003 | Garrec | ..................... | A61K 9/19 424/400 |
| 2007/0082053 A1* | 4/2007 | Kumar | ................. | A61K 31/445 424/486 |

(Continued)

FOREIGN PATENT DOCUMENTS

| | | |
|---|---|---|
| EP | 2 191 830 A1 | 6/2010 |
| WO | WO 2011/110478 A1 | 9/2011 |

OTHER PUBLICATIONS

Waard et al. "A novel bottum-up process to produce drug nanocrystals:Controlled crystallization during freeze-drying". Journal of Controlled Release 128 (2008) 179-183.*

(Continued)

*Primary Examiner* — Robert A Wax
*Assistant Examiner* — Danah Al-Awadi
(74) *Attorney, Agent, or Firm* — Hamilton, Brook, Smith & Reynolds, P.C.

(57) ABSTRACT

The present invention relates to a method of preparation of discrete particles of nanocrystalline solid dispersion, wherein said discrete particle comprises crystals of said active ingredient(s) in the matrix of the said crystallization inducer(s) and/or coexisting with crystals of crystallization inducer(s), optionally along with pharmaceutically acceptable excipient(s). An active ingredient and crystallization inducer is dissolved in a solvent or solvent mixture and then dried to obtain discrete particles of 0.5 to 20 micron size. Each particle consists of crystals of active ingredient in the range of 10-1000 nm dispersed in the matrix of crystallization inducer.

18 Claims, 23 Drawing Sheets

(51) Int. Cl.
*A23L 33/155* (2016.01)
*A23L 33/16* (2016.01)

(56) References Cited

U.S. PATENT DOCUMENTS

| | | | | |
|---|---|---|---|---|
| 2007/0298111 | A1* | 12/2007 | Ueki | A61K 9/1623 424/489 |
| 2008/0274194 | A1 | 11/2008 | Miller et al. | |
| 2009/0012184 | A1 | 1/2009 | Rosenberg et al. | |
| 2011/0014282 | A1* | 1/2011 | de Vasconcelos | A61K 9/145 424/452 |

OTHER PUBLICATIONS

AppaRao, B., et al., "Formulation and Evaluation of Aceclofenac Solid Dispersions for Dissolution Rate Enhancement," *International Journal of Pharmaceutical Sciences and Drug Research*, 146-150 (2010), XP055073086.
Gupta, P., et al., "Molecular interactions in celecoxib-PVP-meglumine amorphous system," *Journal of Pharmacy and Pharmacology*, 57(3): 303-310 (2005).
Onoue, S., et al., "Formulation Design and Photochemical Studies on Nanocrystal Solid Dispersion of Curcumin with Improved Oral Bioavailability," *Journal of Pharmaceutical Sciences*, 99(4):1871-1881 (Apr. 2010).
PCT/IB2013/051807, entitled "Nanocrystalline Solid Dispersion Compositions and Process of Preparation Thereof": International Search Report, dated Dec. 18, 2013.
Punitha, S., et al., "Enhancement of Celecoxib Solubility by Solid Dispersion Using Mannitol," *International Journal of Pharmacy and Pharmaceutical Sciences*, 2(4): 109-111 (2010).
Qian, F., et al., "Mechanistic Investigation of Pluronic (R) Based Nano-crystalline Drug-polymer Solid Dispersions," *Pharmaceutical Research*, 24(8): 1551-1560 (2007).
International Search Report for PCT/IB2013/051807, entitled: Nanocrystalline Solid Dispersion Compositions and Process of Prearation Thereof, dated Dec. 18, 2013.
H. de Waard, et al., "Bottom-up Preparation Techniques for Nanocrystals of Lipophilic Drugs," *Pharm Res.*, 28, 1220-1223 (2011).
H. de Waard, et al., "CLSM as Quantitative Method to Determine the Size of Drug Crystals in a Solid Dispersion," *Pharm Res.*, 28, 2567-2574 (2011).
H. de Waard, et al., "Controlled Crystallization of the Lipophilic Drug Fenofibrate During Freeze-Drying: Elucidation of the Mechanism by In-Line Raman Spectroscopy," *The AAPS Journal*, 12:4 569-575 (Dec. 2010).
H. de Waard, et al., "Preparation of drug nanocrystals by controlled crystallization: Application of a 3-way nozzle to prevent premature crystallization for large scale production," *Eur. J. Pharm. Sci.* 38, 224-229 (2009).
H. de Waard, et al., "A novel bottom-up process to produce drug nanocrystals: Controlled crystallization during freeze-drying," *J. Control. Release*, 128, 179-183 (2008).
de Waard, H., "A Novel Bottom-Up Process to Prepare Drug Nanocrystals: The Art of the Soluble," University of Groningen, Ph.D. Thesis, 2011.
Vig, B. and Morgen, M., "Formulation, Process Development and Scale-Up: Spray Drying Amorphous Solid Dispersions for Insoluble Drugs," Chapter 30, pp. 793-820, in Qiu, Y. *Developing Solid Oral Dosage Forms: Pharmaceutical Theory and Practice*, 2nd edition (2017).
Cavatur, R.K., "Crystallization Behavior of Mannitol in Frozen Aqueous Solutions," *Pharm. Res.*, 19, 894-900 (2002).
Chang, B.S. and Randall, C.S., "Use of Subambient Thermal Analysis to Optimize Protein Lyophilzation," *Cryobiology*, 29, 632-656 (1992).
Chang, L., et al., "Using Modulated DSC to investigate the Origin of Multiple Thermal Transitions in Frozen 10% Sucrose Solutions," *Thermochimica Acta* 444, 141-147 (2006).
Kasraian, K. and DeLuca, P.P., "Thermal Analysis of the Tertiary Butyl Alcohol-Water System and Its Implications on Freeze-Drying," *Pharmaceutical Research*, 12:4 (1995).
Pikal, M.J., "Freeze Drying," in Swarbick, J. "Vol. 1 Encyclopedia of Pharmaceutical Technology Third Edition," 1807-1823 (2006).
Sacha, G.A. and Nail, S.L., "Thermal Analysis of Frozen Solutions: Multiple Glass Transitions in Amorphous Systems," *J. Pharmaceutical Sciences*, 98:9 (Sep. 2009).
Taylor, L.S. and Zografi, G., "Sugar-Polymer Hydrogen Bond Interactions in Lyophilized Amorphous Mixtures," *J. Pharm. Sci.*, 87, 1615-1621 (1998).
Vaka, S.R.K. et al., "Excipients for Amorphous Solid Dispersions" in Shah, N. et al. "Amorphous Solid Dispersions Theory and Practice," Springer (2014).

* cited by examiner

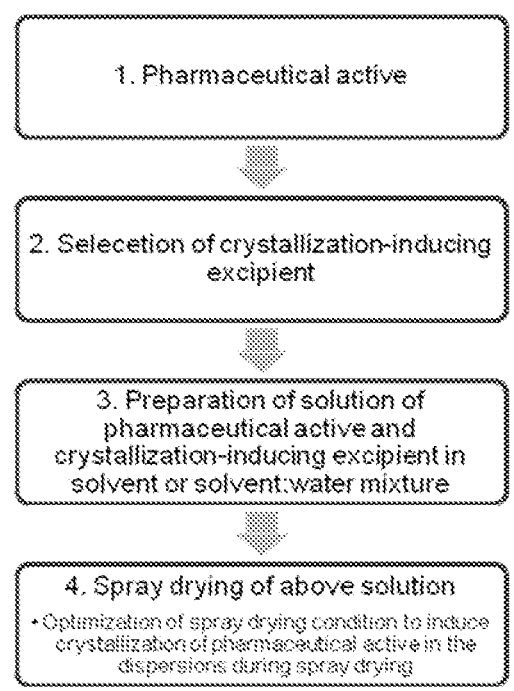
Figure 1: Schematic representation of the process

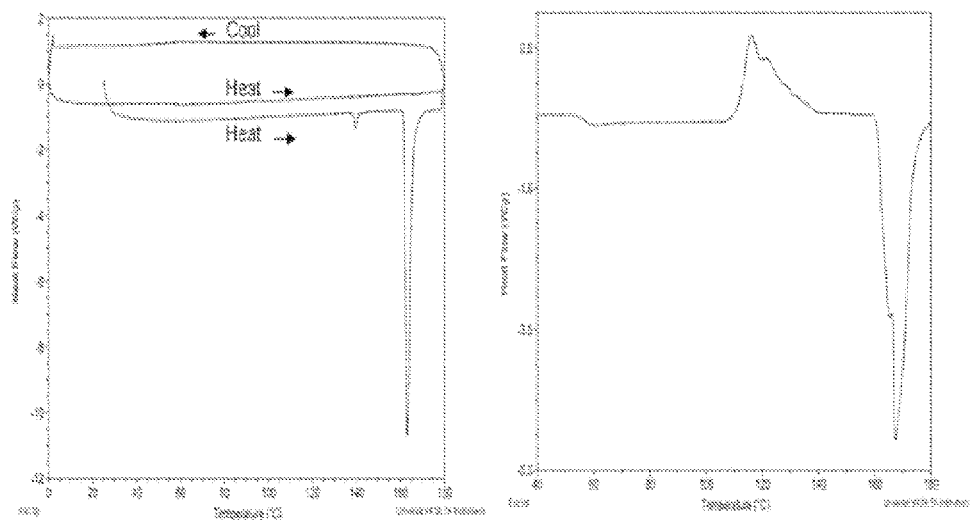
Figure 2: DSC scan of *in-situ* generated amorphous celecoxib (left) and amorphous celecoxib and mannitol physical mixture 50:50 w/w dispersion (right). Amorphous celecoxib shows recrystallization and melting in the presence of mannitol.

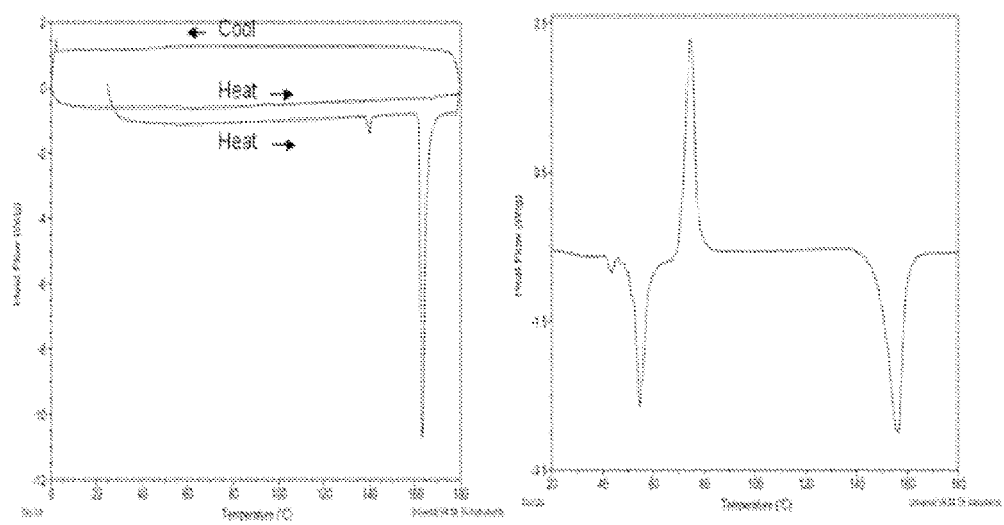
Figure 3: DSC scan of *in-situ* generated amorphous celecoxib (left) and amorphous celecoxib and stearic acid physical mixture 50:50 w/w dispersion (right). Amorphous celecoxib shows recrystallization and melting in the presence of stearic acid.

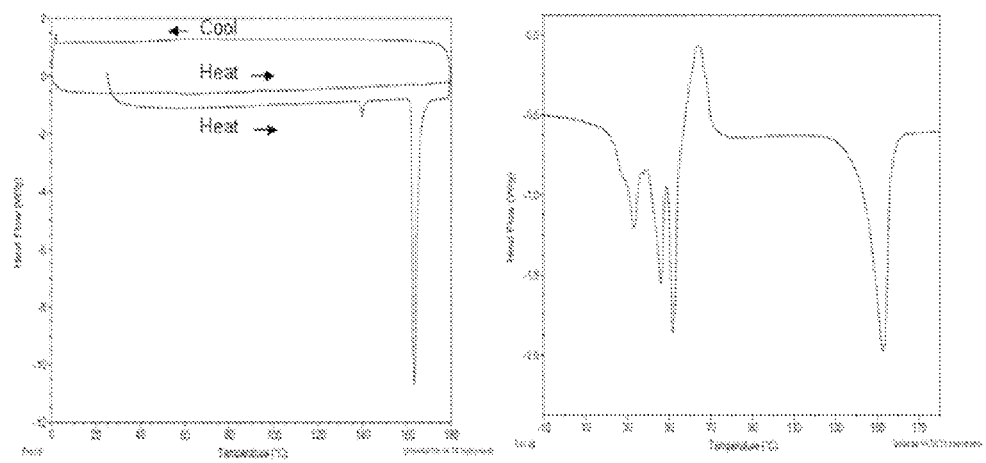
Figure 4: DSC scan of *in situ* generated amorphous celecoxib (left) and amorphous celecoxib and cetostearyl alcohol physical mixture 50:50 w/w dispersion (right). Amorphous celecoxib shows recrystallization and melting in the presence of cetostearyl alcohol.

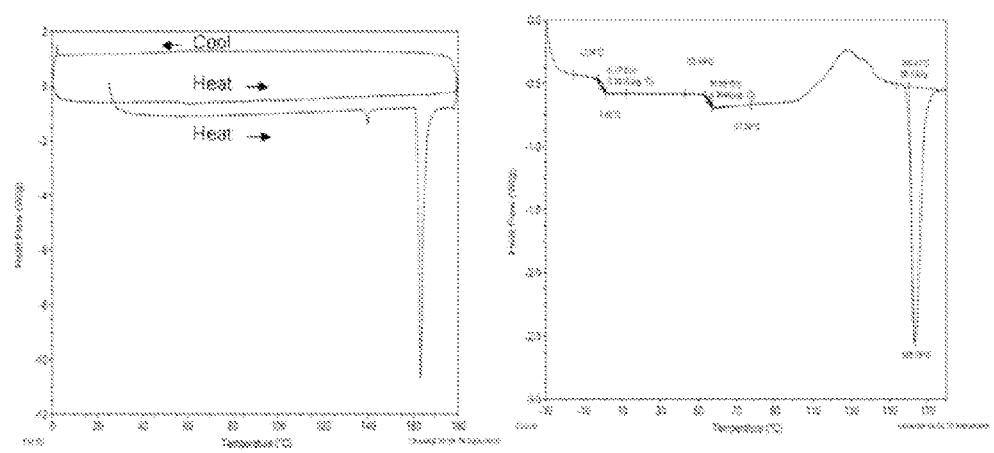

Figure 5: DSC scan of *in-situ* generated amorphous celecoxib (left) and amorphous celecoxib and amorphous sorbitol physical mixture 50:50 w/w dispersion (right). Amorphous celecoxib shows recrystallization and melting in the presence of sorbitol. Dispersion shows two separate $T_g$s, corresponding to sorbitol and celecoxib indicating the immiscibility of two components.

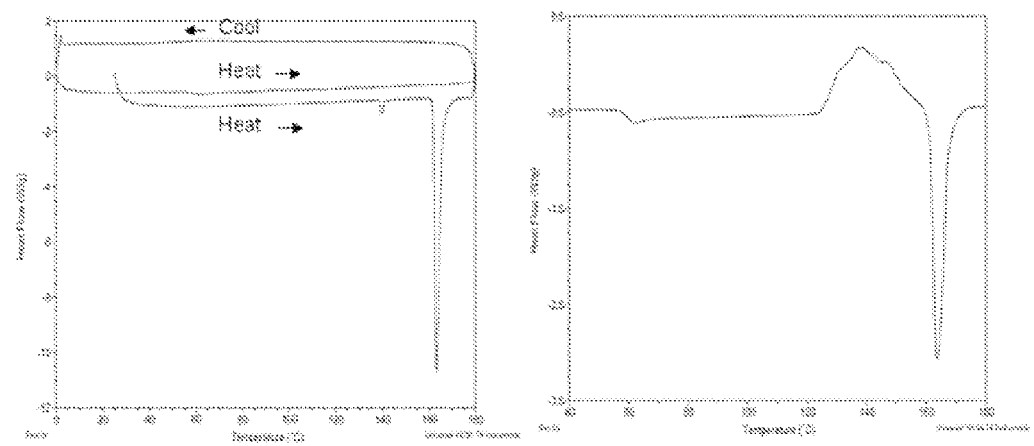
Figure 6: DSC scan of *in-situ* generated amorphous celecoxib (left) and amorphous celecoxib and crystalline potassium chloride physical mixture 50:50 w/w dispersion (right). Amorphous celecoxib shows recrystallization and melting in the presence of potassium chloride.

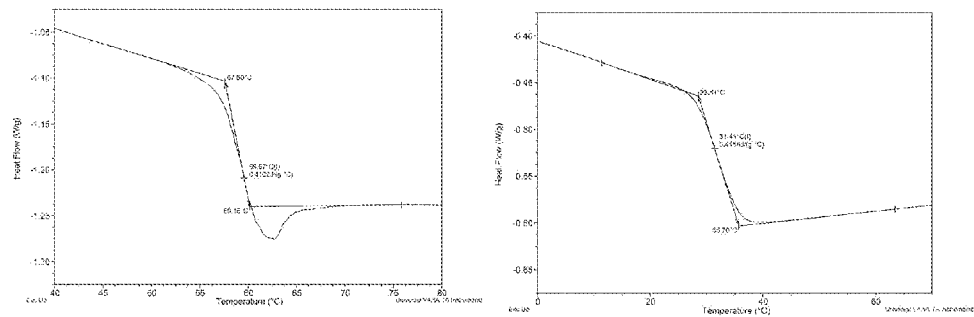
Figure 7: DSC scan of *in-situ* generated amorphous celecoxib (left) and amorphous celecoxib urea 75:25 w/w dispersion (right). Urea causes plasticization of amorphous celecoxib (decrease in $T_g$) and imparts recrystallization followed by melting.

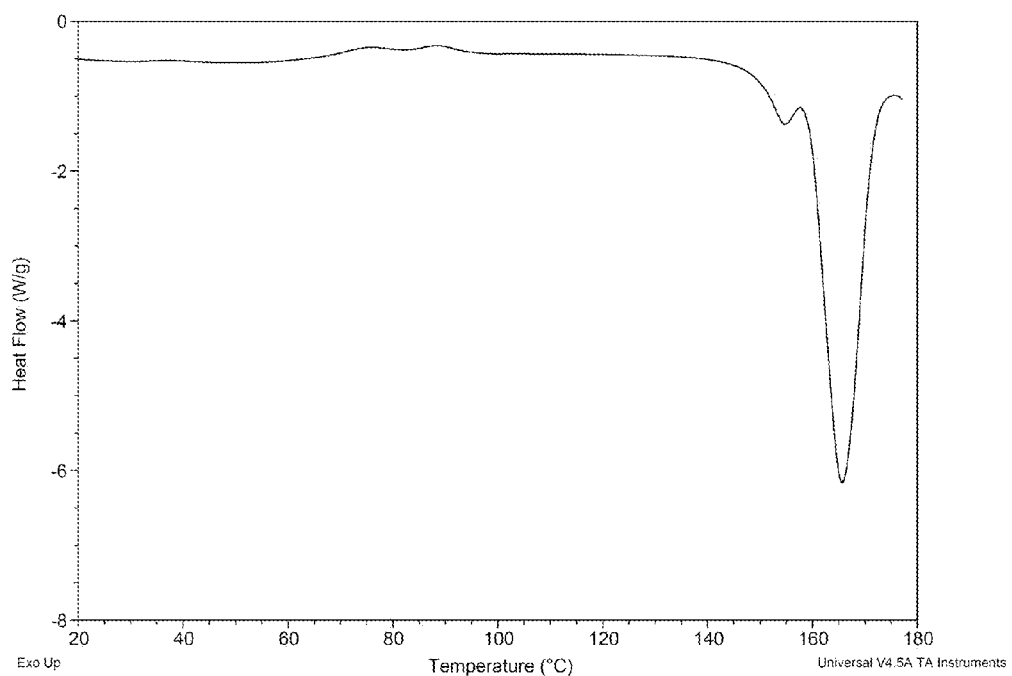
Figure 8: DSC scan of celecoxib: mannitol 50:50 w/w dispersion. Recrystallization and melting is evident for amorphous celecoxib in the presence of mannitol. Melting of mannitol is also visible.

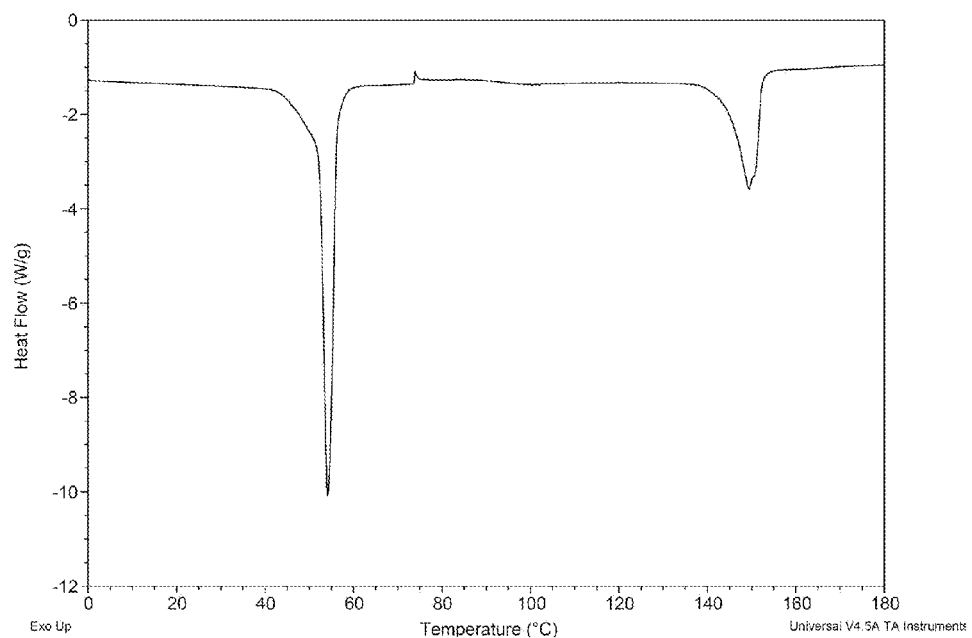
Figure 9: DSC scan of celecoxib: stearic acid 50:50 w/w dispersion. Recrystallization and melting is evident for amorphous celecoxib in the presence of stearic acid. Melting of stearic acid is also visible.

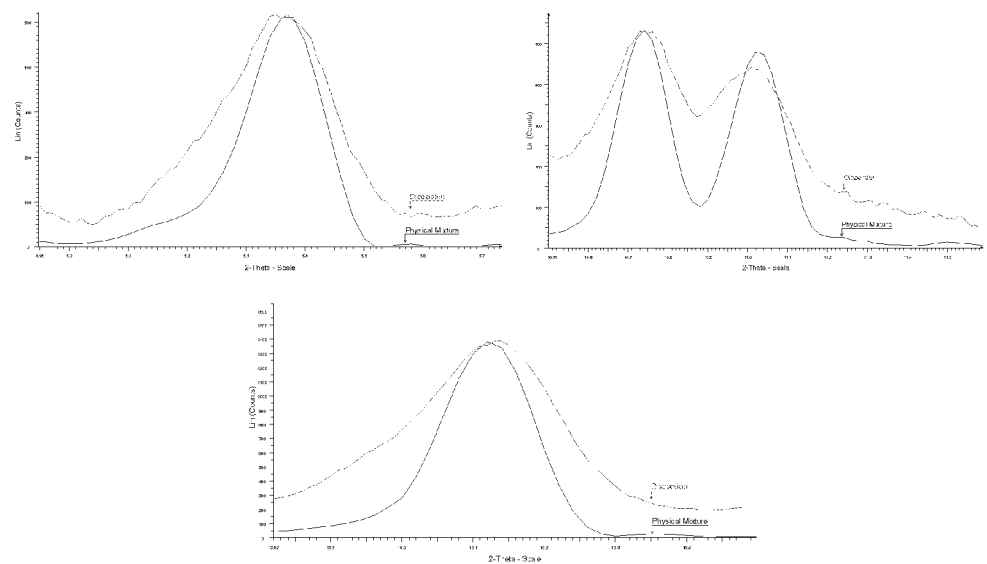
Figure 10: Representative broadening of PXRD peaks of celecoxib in celecoxib: stearic acid dispersion

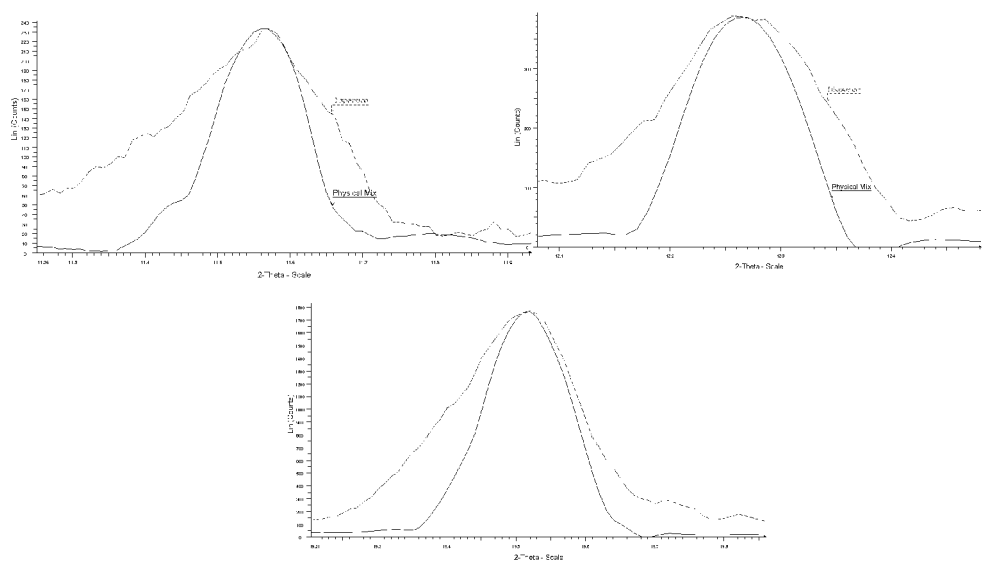
Figure 11: Representative broadening of PXRD peaks of aceclofenac in aceclofenac: potassium chloride dispersion

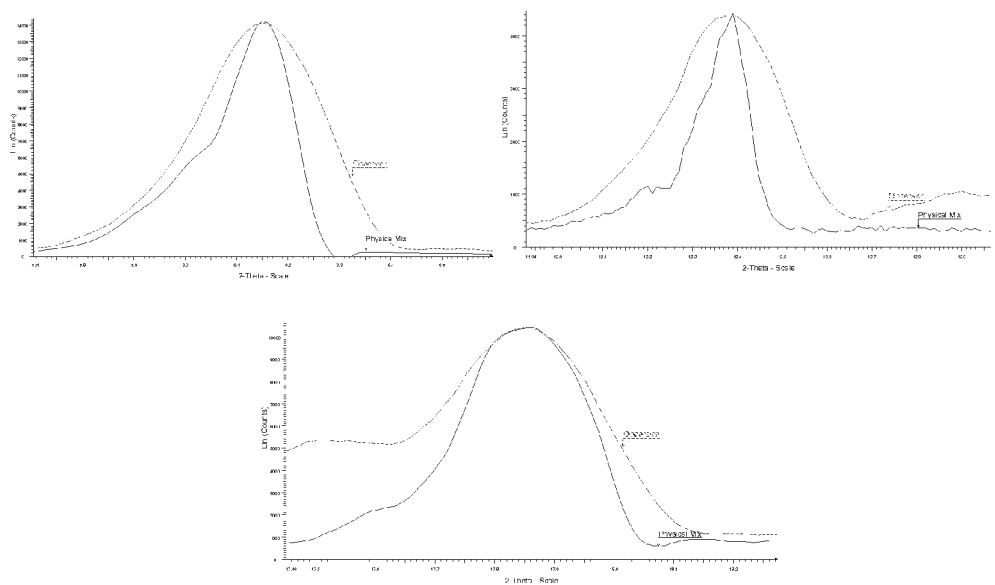
Figure 12: Representative broadening of PXRD peaks of Ibuprofen in ibuprofen mannitol dispersion

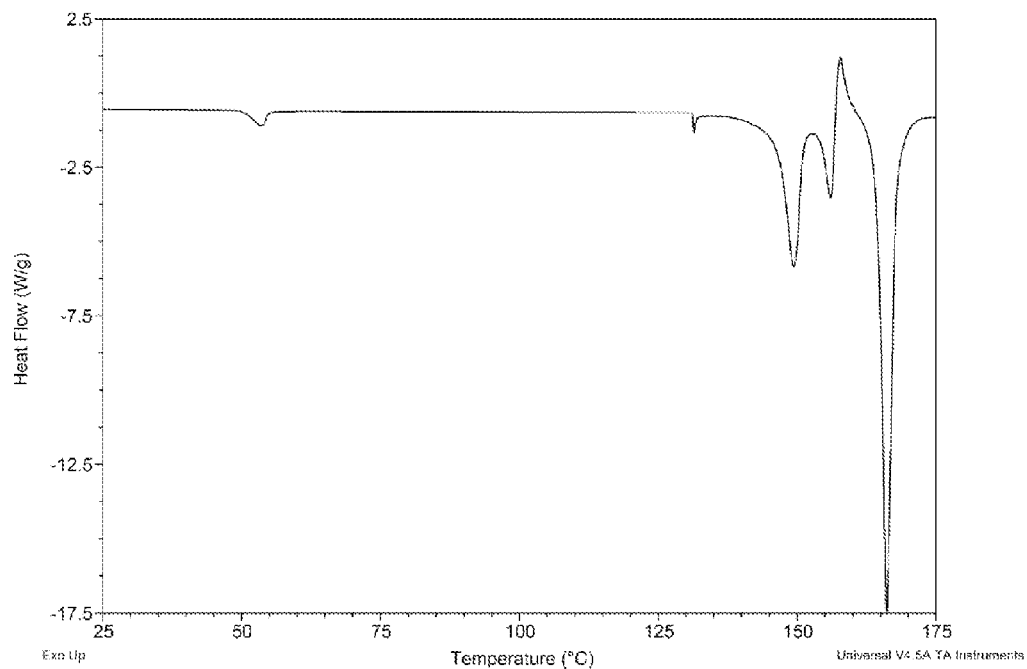
Figure 13: DSC scan of Aceclofenac: Stearic acid dispersion 50:50 w/w. Recrystallization and melting is evident for amorphous celecoxib in the presence of stearic acid. Melting of stearic acid is also visible.

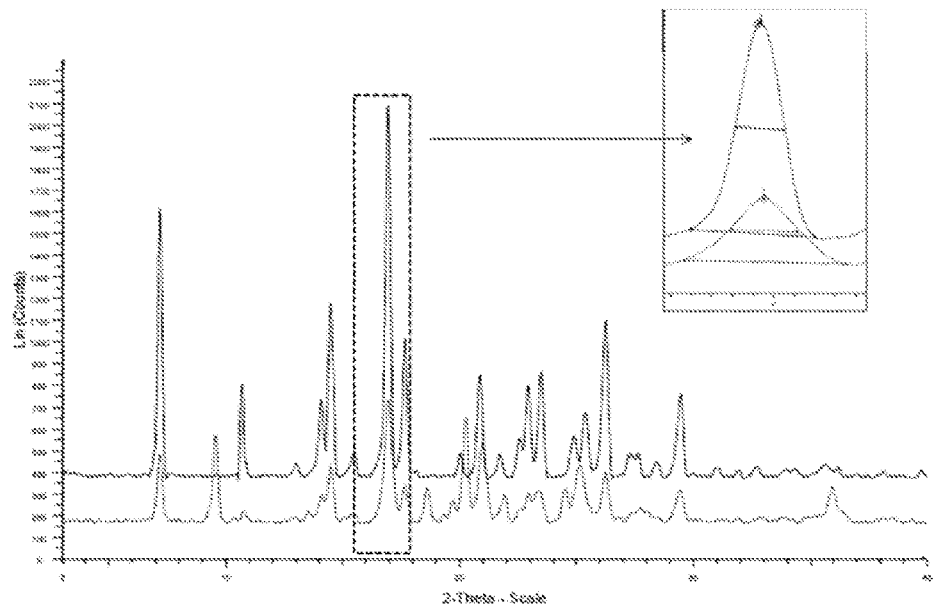
Figure 14: PXRD of hesperetin and its nanocrystalline solid dispersion with mannitol in 50:50 w/w proportion; inset depicts measurement of peak width at half height.
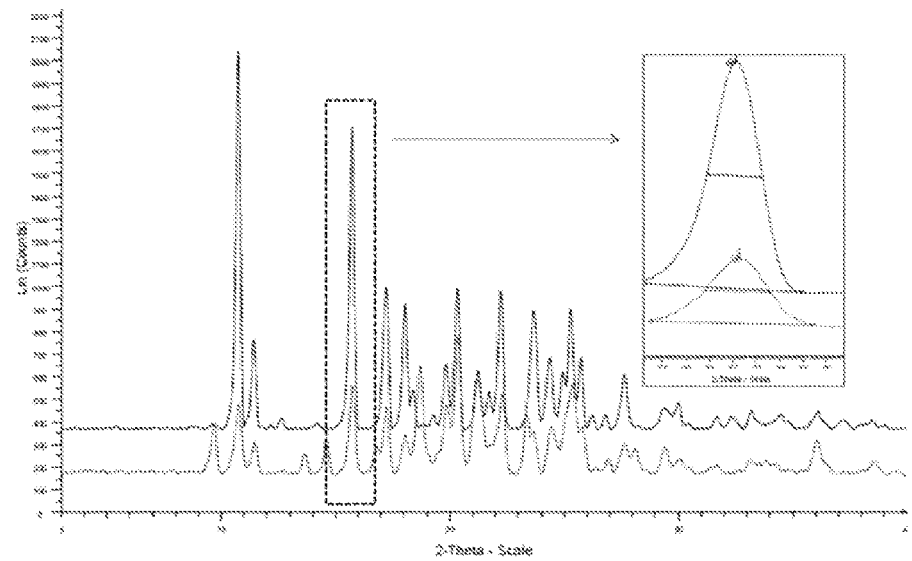
Figure 15: PXRD of naringenin and its nanocrystalline solid dispersion with mannitol in 50:50 w/w proportion; insect depicts measurement of peak width at half height

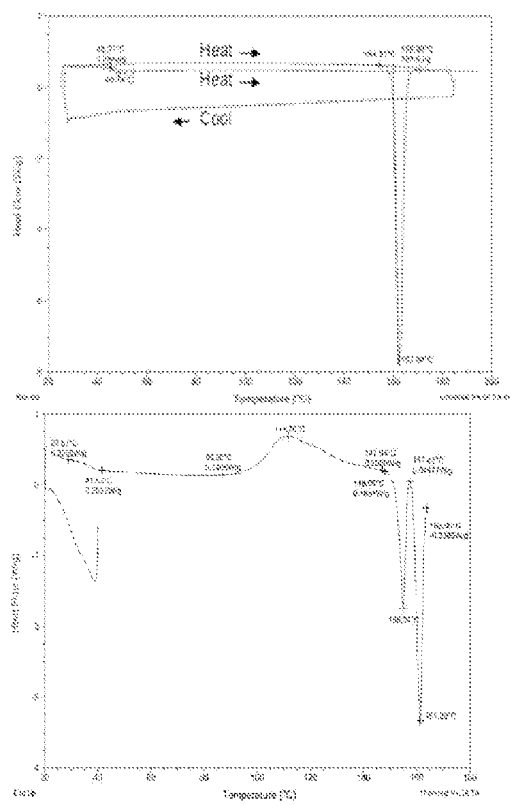
Figure 16: DSC scan of indomethacin: mannitol 50:50 w/w dispersion. Recrystallization and melting is evident for amorphous indomethacin in the presence of mannitol. Melting of mannitol is also visible.

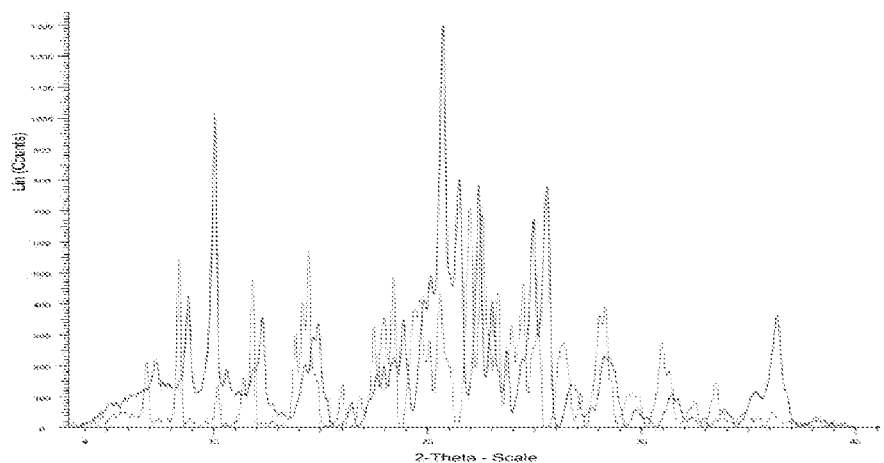
Figure 17: PXRD of indomethacin and its nanocrystalline solid dispersion with mannitol in 50:50 w/w proportions

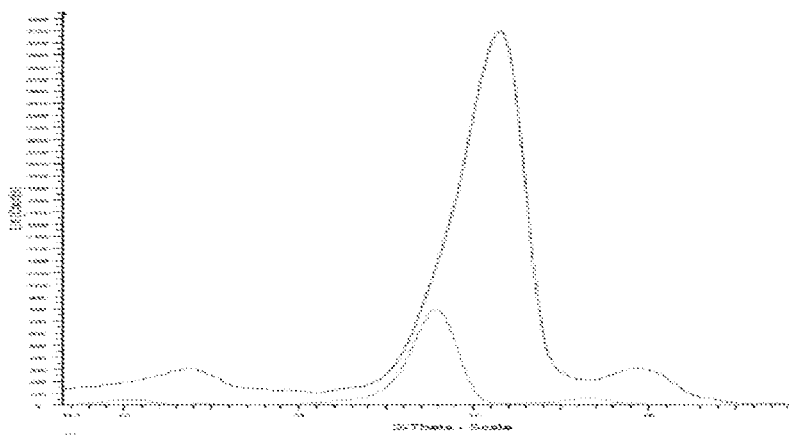
Figure 18: Representative broadening of PXRD peaks of curcumin in curcumin : mannitol dispersion

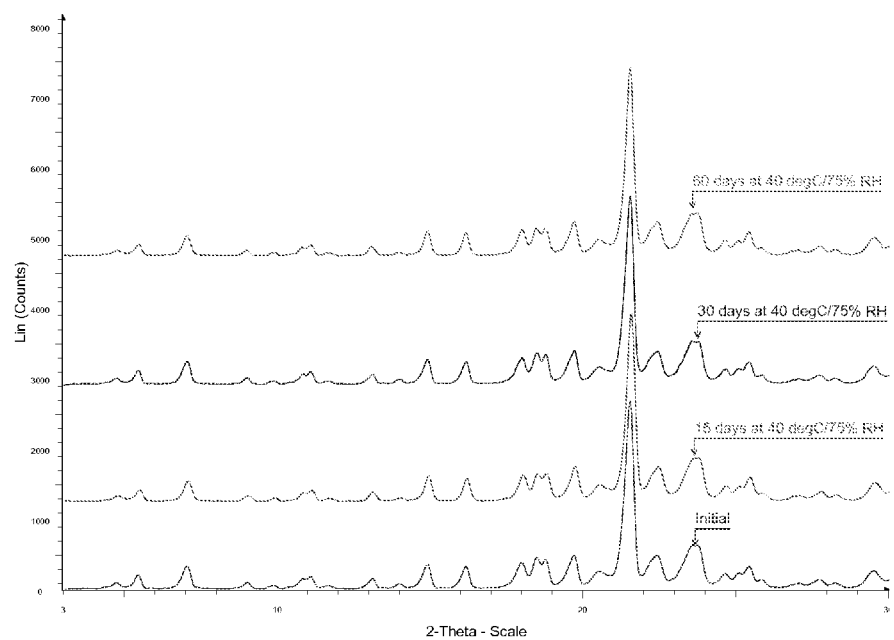
Figure 19: PXRD overlay of Accelerated stability (40 °C/75% RH) samples of Celecoxib: Stearic acid 50:50 % w/w nanocrystalline solid dispersion. No significant change in the PXRD patterns indicates physical stability of dispersion.

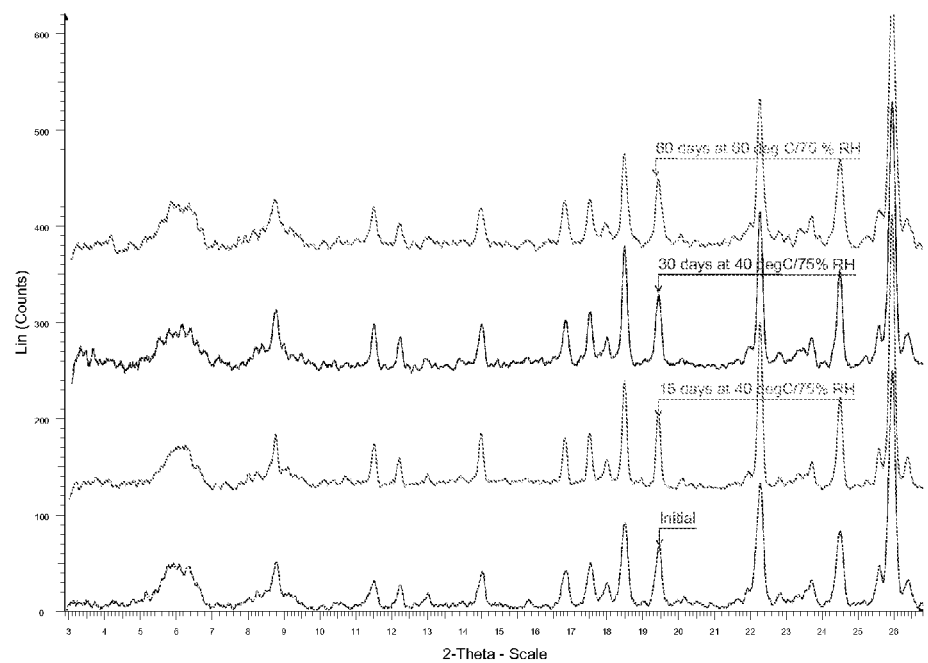
Figure 20: PXRD overlay of Accelerated stability (40 °C/75% RH) samples of Aceclofenac: Potassium Chloride 50:50 % w/w nanocrystalline solid dispersion. No significant change in the PXRD patterns indicates physical stability of dispersion.

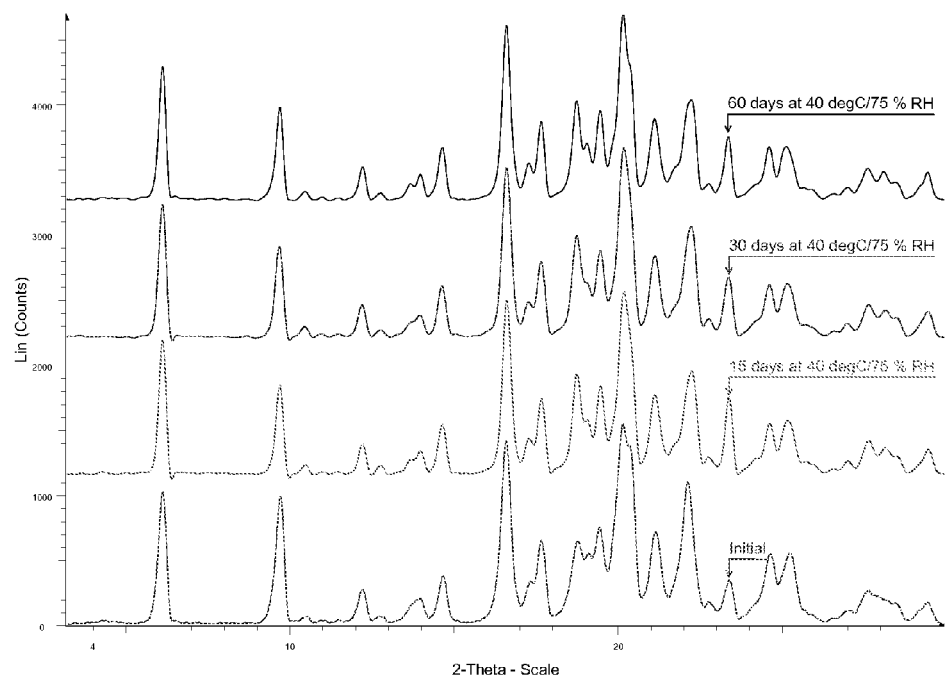
Figure 21: PXRD overlay of Accelerated stability (40 °C/75% RH) samples of Ibuprofen: Mannitol 50:50 % w/w nanocrystalline solid dispersion. No significant changes in the PXRD patterns indicate physical stability of dispersion.

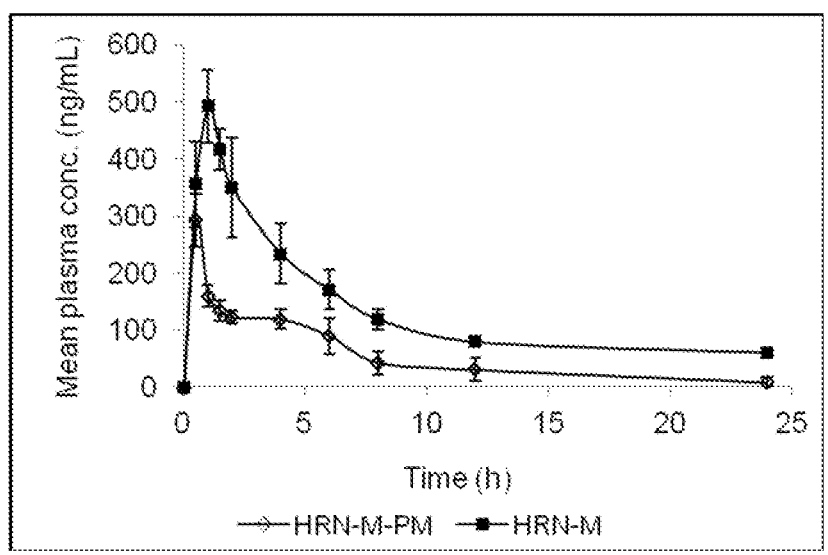
Figure 22. Mean plasma concentration-time profile of HRN-M-PM and HRN-M

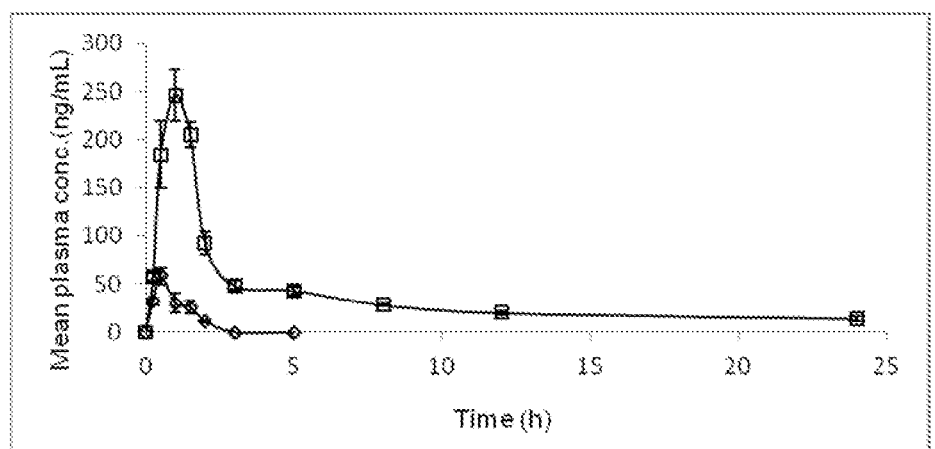
Figure 23. Mean plasma concentration-time profile of control (◊) and Curcumin stearic acid NSD (CRM-SA) (□)

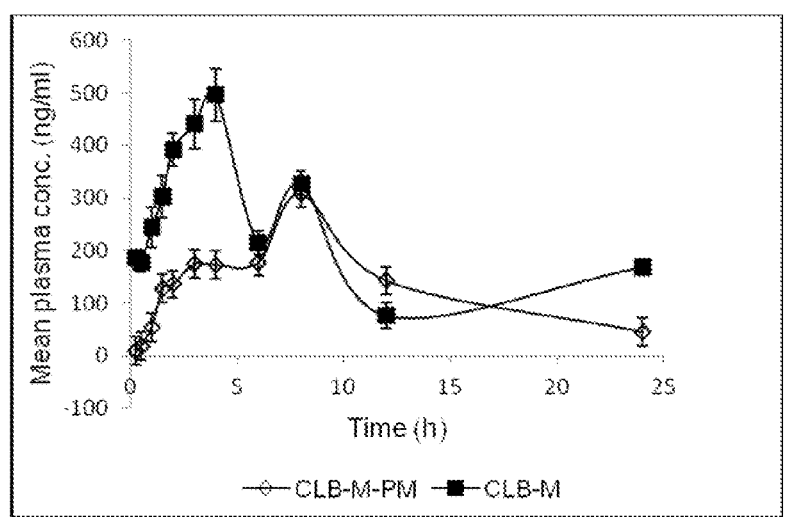
Figure 24. Mean plasma concentration-time profile of celecoxib mannitol physical mixture (CLB-M-PM) and their nanocrystalline solid dispersion (CLB-M)

NANOCRYSTALLINE SOLID DISPERSION COMPOSITIONS AND PROCESS OF PREPARATION THEREOF

RELATED APPLICATION(S)

This application is the U.S. National Stage of International Application No. PCT/IB2013/051807, filed Mar. 7, 2013, which designates the U.S., published in English, and claims priority under 35 U.S.C. §§119 or 365 to Indian Application No. 0674/DEL/2012, filed Mar. 7, 2012. The entire teachings of the above applications are incorporated herein by reference.

The following specification particularly describes the invention and the manner in which it is to be performed.

FIELD OF THE INVENTION

The present invention relates to novel one step process for the preparation of compositions comprising nanocrystalline solid dispersions. More particularly present invention focuses on use of a crystallization inducer and pharmaceutical active to make compositions with enhanced dissolution rate of pharmaceutical active.

BACKGROUND OF INVENTION

Solubility and dissolution rate issues still remain a challenge to the pharmaceutical scientists. These difficulties are more apparent with hydrophobic drugs, and with high number of hydrophobic drugs entering the drug discovery and product development pipeline, these issues become even more important to settle. Pharmaceutical actives belonging to Biopharmaceutics Classification System (BCS) class II and IV present solubility-related challenges in formulation development. Strategies for improving apparent solubility and dissolution rate include forming soluble salts for ionizable drugs, reducing crystal size, forming soluble pro-drugs, using amorphous forms, co-solvents and super disintegrants, and using surface active self-emulsifying systems.

With most sophisticated size reduction technologies being developed in recent years, size reduction to nanoparticles has attracted lot of attention in the formulation development of hydrophobic drugs. Nanoparticles can be generated by many means, like top-down approaches such as size reduction by advanced milling techniques or by bottom-up approaches like precipitation. However, due to small size and high surface area, the dispersion of the nanoparticles in the dissolution media often remains a challenge and requires addition of surface modifying agents to reduce the agglomeration tendency and increase the dispersability. A solid dispersion contains at least two components: a matrix and a pharmaceutical active ingredient. The matrix can be either amorphous or crystalline, and the drug can be dispersed within the matrix as an amorphous molecular dispersion or as amorphous particles or as nanosized crystals. Amorphous solid dispersion of insoluble pharmaceutical active in high molecular weight water-soluble polymeric matrices is reported to be highly efficient as it presents the pharmaceutical active at the molecular level to the dissolution media (U.S. Pat. No. 7,713,548). Amorphous solid dispersions are usually prepared by spray drying, by depositing drug solution onto the carrier in a fluidized bed granulator, by melt extrusion, by melt fusion, twin-screw extruder, evaporation, curing, microwaving, milling, ultra sound, spinning by mechanical admixture such as by ball milling and by mechanical admixture at an elevated but non-melting temperature.

Most common technique of generation of amorphous solid dispersion is solvent method that involves dissolution of the drug/pharmaceutical active and matrix material in a solvent. The solvent is then removed to leave a mixture of drug and matrix in solid form. Further solvent can be removed by vacuum drying, spray drying and freeze drying.

Commercialization of amorphous solid dispersion is still a challenge due to unpredictable physical stability of the amorphous pharmaceutical active (*Critical Reviews™ in Therapeutic Drug Carrier Systems*, 21(3):133-193 (2004)) and atypical dissolution behavior of amorphous dispersion dosage forms (*Journal of Pharmaceutical Sciences* 100(6): 2460-2468 (2011)). Problems with chemical stability due to interaction between drug-polymer matrixes also add to the complication. Phase separation due to external stresses during various manufacturing unit operations has to be monitored thoroughly for the success of amorphous solid dispersions. Most of the excipients used in the solid dispersions are polymeric in nature. Polymeric excipients result in drug being at least partially converted to amorphous form.

Latter has higher energy and undergoes recrystallization during shelf-life. Amorphous form also undergoes recrystallization during dissolution stage. It is hence difficult to predict the performance of the drug present in amorphous form. Dosage forms prepared using amorphous form also pose problems like recrystallization during processing, poor dispersability and retarded dissolution kinetics. Moreover, polymers generally are hygroscopic in nature and recent reports indicate this hygroscopic nature is detrimental to the stability of the amorphous solid dispersions, as moisture uptake by the polymers may lead to the phase separation which further may lead to physical instability of amorphous drug. Crystalline solid dispersions of the present invention, on other hand, offer advantage of higher dissolution rate compared to "raw" or "untreated" drug/pharmaceutical active.

Reference may be made to U.S. Pat. No. 5,456,923 discloses an invention comprising of employing a twin-screw extruder in the production of a solid dispersion. In accordance with the invention, a solid dispersion can be expediently produced without heating a drug and a polymer to or beyond their melting points and without using an organic solvent for dissolving both components.

In yet another reference U.S. Pat. No. 6,706,283 discloses an invention comprising of controlled release dosage forms for low solubility drugs, wherein an amorphous solid dispersion of the drug is coated with a non-dissolving and non-eroding coating that controls the influx of water to the core so as to cause extrusion of a portion of the core.

In another reference US 2009/0285905 discloses a pharmaceutical composition comprising of hydrophobic drug and hydrophilic components and spray drying them simultaneously in a spray dryer for uniform dry powder characteristics for inhalation drug delivery. The hydrophilic components used in the invention varied in their properties, which would affect the physical form of drug in the final product. The physical form of the drug in the final product, in the invention, is ill-defined.

WO 2010/133611 discloses an invention comprising of preparation of solid dispersion of drug with super disintegrant. The preparation comprises the steps of providing a crystalline drug in which the drug crystals have a median diameter $U_{50\%}$ of not generally more than 20, preparing a dispersion or suspension of drug crystals in a disintegrant solution or suspension, and spray drying the dispersion or suspension to provide a solid crystalline drug dispersion.

U.S. Pat. No. 6,932,983 discloses an invention comprising of providing a low aqueous solubility drugs in a porous matrix form, preferably microparticles, to enhances dissolution of the drug in aqueous media U.S. Pat. No. 4,721,709 discloses pharmaceutical compositions containing hydrophobic practically water-insoluble drugs adsorbed onto carriers such as starch and/or microcrystalline cellulose. The rate of dissolution and absorption in the body is improved due to the very fine particle size of the drug adsorbed onto the carriers.

US 2009/0098200 discloses a pharmaceutical composition of hydrophobic drug interwoven with a polymeric matrix formed by two or more polymers, wherein one of the polymers is an amphiphilic polymer and the other polymer is either an amphiphilic polymer with a different hydrophobic-hydrophilic balance or a hydrophilic polymer, and the active hydrophobic drug has modified physicochemical properties. The composition forms colloidal nanodispersion upon contact with aqueous media. The hydrophobic drug is either in crystalline or amorphous form in the final product. However, the presence of amorphous hydrophobic drug could cause physical instability during the shelf-life. Presence of amorphous form of hydrophobic drug in the final product would also induce interactions with polymers which may lead to chemical instability.

US 2007/0134340 discloses an invention which provides the process of preparation of nanocrystals or polymer doped nanocrystals of hydrophobic drug molecules as stably dispersed in an aqueous system which are prepared without stabilizers like surfactants and the like. Drug efficacy of these nanocrystals was found to be comparable with that of same drug formulated in conventional delivery vehicles under in vitro and in vivo conditions.

In WO/1997/013503 a method of synthesizing nanoparticles composites by combining an agent and a matrix to form a composite mixture in an organic solvent or solvent/water is disclosed further mixture was spray dried to remove the solvent. Here the matrix used is mannitol. Type of matrix material, spray drying conditions and properties of the agent determine the solid form being formed.

In yet another reference U.S. Pat. No. 5,976,574 method for preparing dry powders having hydrophobic and hydrophilic components is disclosed. The process comprises combining solutions or suspensions of the components and spray drying them simultaneously in a spray drier. The hydrophobic component may be dissolved in an organic solvent and the hydrophilic component suspended therein wherein the hydrophilic component used is mannitol. This prior art mentions use of solubilizing the hydrophobic drug in a solvent and suspending the hydrophilic excipient in the solution. The resultant dispersion is spray dried to obtain coating of hydrophilic particles with hydrophobic drug. The method relies on separation of submicron particles by using separation techniques like cyclone separator. In compare, present invention uses a solution of the active agent and matrix forming agent wherein the latter acts as a crystallization inducer for the active agent. Crystallization during spray drying happens to achieve nanocrystalline state of active agent in the matrix of the crystallization inducing excipient.

In yet another reference U.S. Pat. No. 5,985,248 preparation of dry powder compositions is disclosed. In particular, spray drying method which permits simultaneous spray drying of the hydrophobic component with a hydrophilic component, such as a hydrophilic pharmaceutical excipient, under conditions which result in a dry powder comprising mixtures of both the hydrophilic and hydrophobic components. This prior art document discloses use of solution of hydrophobic agent and hydrophilic agent in a common solvent/solvent system. The resultant solution is spray dried to achieve individual particles in the submicron range. The spray dried product is further broken down into smaller particles using appropriate de-agglomeration tools like size screening. Thus, prior art in no way enables present invention wherein essentially nanocrystalline active is produced due to use of crystallization inducing excipient during the spray drying process.

In yet another reference WO/2007/136830 a process for producing particles comprising, preparing a solution of a compound with at least one solvent; spraying the solution into a chamber under conditions that allow for a substantial amount of the solvent to be removed from said solution, such that particles of said compound have a mean diameter of less than or equal to 3000 nm. This prior art describes spray drying of API solution to obtain particles of pure API. This is not relevant to our invention, as it deals with generation of nanocrystalline solid dispersion in presence of crystallization inducing excipient.

In review article titled "A review on drug nanocrystal a carrier free drug delivery" by; Patel Anita P; various methods for the production of drug nanocrystals are disclosed like a method wherein drug nanosuspensions are spray dried, and the nanosuspensions are formed by mixing drug with sugar alcohols like mannitol. This article describes details about nanocrystals present in suspended form in a solvent system. It also mentions carrier free drug delivery system in suspension, whereas present invention mentions preparation of nanocrystals in dry form along with a carrier such as mannitol.

Another reference titled "Nanoparticle Formulation for Hydrophilic & Hydrophobic Drugs" by Vivek Kumar Gupta discloses the production of nano particles of drug, by spray drying in the presence of sugar excipients such as lactose and mannitol. This document talks about preparation of nano particulate drug delivery system formed an intact structure of polymers with API distributed in it. Polymeric matrix forming agents usually form amorphous solid dispersions, as they impede crystallization of active, by decreasing molecular mobility, by virtue of their high viscosity. In comparison, present invention deals with use of crystallization inducing agent to produce nanocrystalline solid dispersion.

Thus the above references do not enable formation of nanocrystalline solid dispersion whereas present invention relates to formation of nanocrystalline solid dispersion, by inclusion of crystallization inducing excipient.

Existing drawbacks in available art, like multi-step process for the preparation and ill-defined physical form etc. that affect the biopharmaceutical properties during their shelf-life have been overcome by the present invention.

OBJECT OF THE PRESENT INVENTION

The main object of the present invention is to provide a novel one step process for the preparation of compositions comprising nanocrystalline solid dispersions.

Another object of the present invention is to provide a composition comprising of nanocrystalline solid dispersions, with enhanced dissolution rate of pharmaceutical active.

SUMMARY OF THE INVENTION

The present invention relates to novel one step process for the preparation of compositions comprising nanocrystalline solid dispersions. More particularly present invention focuses on use of a crystallization inducer and pharmaceutical active to make compositions with enhanced dissolution rate of pharmaceutical active.

Accordingly, the invention provides a one-step process for preparation of compositions comprising a pharmaceutical active and a crystallization-inducing excipient in a discrete particulate form, wherein each discrete particle comprises of pharmaceutical active in nanocrystalline form dispersed in matrix of crystallization inducer and/or coexisting with crystals of crystallization-inducing excipients. In instant invention a solution of pharmaceutical active drug and crystallization-inducing excipient in solvent or solvent mixture are dried to obtain solid composition. Spray drying would be preferred technique of drying over other conventional techniques like vacuum drying, and freeze drying etc. because of cost effective scalability of drying step. Spray drying of pharmaceutical active-crystallization-inducing excipients solution would yield discrete particles in the micron-size range. Size of the particles is predominantly in the range of 0.5 to 20 micron, preferably in the range of 1 to 10 micron more preferably in the range of 2-8 micron. Each discrete particle of the composition is comprised of crystals of pharmaceutical active dispersed in matrix of crystallization-inducing excipients or coexisting with crystals of crystallization-inducing excipient. The size of the crystals of pharmaceutical active is in the range of 10-2000 nm. The spray drying method of the present invention is optimized in such a way that drying temperature is higher than the crystallization temperature of the components, i.e., pharmaceutical active drug and crystallization-inducing excipient of the composition.

One embodiment of the present invention provides pharmaceutical composition in powder form comprising discrete particles in micron-size range, wherein each discrete particle comprises crystals of at least one pharmaceutical active, dispersed in the matrix of at least one crystallization inducer and/or coexisting with crystals of crystallization inducer.

In another embodiment of the present invention provides applicability to encompass a composition containing more than one pharmaceutical active and/or more than one crystallization inducer.

In another embodiment of the present invention, the composition comprises of pharmaceutical active in the range of 0.01% to 95% of the powder, and the crystallization-inducing excipient, usually present in the range of 99.99% to 5% of the powder.

In a yet another embodiment of the present invention the composition is preferably veterinary composition, in powder form comprising discrete particles in micron-size range, wherein each discrete particle comprises crystals of at least one veterinary active dispersed in the matrix of at least one crystallization inducer and/or coexisting with at least one crystal of crystallization inducer.

In a yet another embodiment of the present invention, the composition may extend its applicability to encompass a composition containing more than one veterinary active and/or more than one crystallization inducer.

In a yet other embodiment of the present invention, the composition comprises of veterinary active in the range of 0.01% to 95% of the powder, and the crystallization-inducing excipient, usually present in the range of 99.99% to 5% of the powder In yet another embodiment of the present invention the composition is preferably a nutraceutical composition, in powder form comprising discrete particles in micron-size range, wherein each discrete particle comprises crystals of at least one nutraceutical dispersed in the matrix of at least one crystallization inducer and/or coexisting with crystals of at least one crystallization inducer.

In yet another embodiment of the present invention, the composition may extend its applicability to encompass a composition containing more than one nutraceutical and/or more than one crystallization inducer.

In yet another embodiment of the present invention, the composition comprises of nutraceutical in the range of 0.01% to 95% of the powder, and the crystallization-inducing excipient, usually present in the range of 99.99% to 5% of the powder In yet another embodiment of the present invention, the pharmaceutical composition is comprised of a pharmaceutical active wherein the said pharmaceutical active comprises of hydrophilic or hydrophobic pharmaceutical active.

In yet another embodiment of the present invention, the pharmaceutical composition is preferred for dissolution enhancement of hydrophobic pharmaceutical active.

In yet another embodiment of the present invention, the pharmaceutical composition wherein said pharmaceutical active can be hydrophobic pharmaceutical active having either dissolution-limited or solubility-limited or solubility and dissolution-limited absorption.

In yet another embodiment of the present invention, the pharmaceutical composition wherein said hydrophobic pharmaceutical active is selected from the group consisting of all classes of drugs. Preferred examples of hydrophobic drugs included but not limited to celecoxib, aceclofenac, nateglinide and ibuprofen.

In yet another embodiment of the present invention, the veterinary composition comprises a veterinary drug selected from the group consisting of albendazole, fenbendazole and itraconazole.

In yet another embodiment of the present invention, the nutraceutical composition comprises resveratrol or hesperetin as the nutraceutical.

In yet another embodiment of the present invention, the said crystallization-inducing excipient comprises excipients which induce the crystallization tendency of either the pharmaceutical active or veterinary active or nutraceutical by decreasing the crystallization temperature of the pharmaceutical active.

In yet another embodiment of the present invention, the said crystallization inducer comprises an example selected from the group consisting of mannitol potassium chloride etc., salts thereof, and hydrates thereof.

In another embodiment of the present invention a process for the preparation of a composition comprising the steps of: (i) preparing a clear and homogeneous solution of crystallization-inducing excipient and the at least one pharmaceutical active compound in a mixture of water and an organic solvent or organic solvent alone; and (ii) drying the clear and homogeneous solution of crystallization-inducing excipients-pharmaceutical active of (i), to form a dry powder.

In yet another embodiment of the present invention wherein the drying in step (ii) is carried out by conventional drying techniques like spray drying, vacuum drying, solvent evaporation etc.

In yet another embodiment of the present invention wherein the clear solution of crystallization-inducing excipients-pharmaceutical active clear and homogeneous solution is obtained by preparing a solution of the pharmaceutical active in an organic solvent, adding the clear solution of crystallization-inducing excipients in organic solvent or aqueous media or aqueous-solvent mixture to the pharmaceutical active organic solution, and said organic solvent is selected from the group consisting of alcohols, ketones, ethers, aldehydes, hydrocarbons and polar aprotic solvents and mixtures thereof.

In yet another embodiment, the present invention preferably comprise of spray-dried particles.

In yet another embodiment of the present invention wherein at least about 90% by number of the discrete particles have the average particle size within a micron-range, and each discrete particle having the pharmaceutical active crystalline fog, 1, within a range from 10 to 1000 nm.

In yet another embodiment of the present invention wherein the hydrophobic drug comprises a non-steroidal anti-inflammatory drug (NSAID) and crystallization-inducing excipient comprises a polyol.

In yet another embodiment of the present invention wherein the said NSAID is ibuprofen and crystallization-inducing excipient is mannitol.

In yet another embodiment of the present invention wherein a process for the preparation of a composition comprising the steps of: (i) preparing a clear and homogeneous solution of mannitol and Ibuprofen separately in water and methanol and then mixing both the solutions; and (ii) drying the clear and homogeneous solution of crystallization-inducing excipients-pharmaceutical active of (i) to form a dry powder.

In yet another embodiment of the present invention wherein preferred drying technique is spray drying.

In yet another embodiment of the present invention wherein the discrete particles comprises spray-dried particles.

In yet another embodiment of the present invention wherein at least about 90% by number of the discrete particles have the average particle size within micron-range having the crystals of pharmaceutical active within a range from 10 to 2000 nm, more especially in the range of 10-1000 nm.

In yet another embodiment of the present invention wherein said hydrophobic drug comprises an anti-diabetic drug and crystallization-inducing excipient comprising an inorganic salt.

In yet another embodiment of the present invention wherein the said anti-diabetic is nateglinide and crystallization-inducing excipients is potassium chloride.

In yet another embodiment of the present invention a method for the preparation of a composition comprising the steps of: (i) preparing a clear and homogeneous solution of potassium chloride and nateglinide separately in water and methanol respectively and then mixing both the solutions; and (ii) drying the clear and homogeneous solution of crystallization-inducing excipients-pharmaceutical active of (i) to form a dry powder.

In yet another embodiment of the present invention preferred drying technique is spray drying.

In yet another embodiment of the present invention wherein the discrete particles comprise spray-dried particles.

In yet another embodiment of the present invention wherein at least about 90% by number of the discrete particles have the average particle size within micron-range having the crystals of pharmaceutical active within a range from 10 to 2000 nm, more especially in the range of 10-1000 nm.

In yet another embodiment of the present invention wherein composition is designed for release of the pharmaceutical active either in gastro-intestinal tract, preferably a composition that has higher biopharmaceutical performance upon contact with gastro-intestinal fluids.

In yet another embodiment of the present invention wherein the composition is stable against crystal growth of pharmaceutical active within shelf-life and does not exhibit any changes in the chemical or physicochemical properties, particularly exhibiting enhanced dissolution rate, when hydrophobic pharmaceutical active and water-soluble crystallization inducing excipient are the components of the composition.

In yet another embodiment of the present invention the composition additionally consisting of pharmaceutical excipient to enhance solubility/dissolution, stability and permeability; preferably belonging to the class of solubilizers, pH modifying agents, surfactants and desiccants.

The drawback of multi step-processes of the prior art is addressed by developing knowledge based selection of crystallization inducing excipients and processing parameters.

The drawback of ill-defined physical form in the final product of the prior art is addressed by proposing specific condition for inducing crystallization of both the components of the composition. The product obtained by the method of the present disclosure has both the components in crystalline form.

BRIEF DESCRIPTION OF THE ACCOMPANYING DRAWINGS OR FIGURES

The accompanying drawings illustrate embodiments of the invention and, together with the description, serve to explain the invention. These drawings are offered by way of illustration and not by way of limitation.

FIG. 1 shows the schematic representation of process of the present invention.

FIG. 2 shows DSC scan of in-situ generated amorphous celecoxib (left) and amorphous celecoxib and mannitol physical mixture 50:50 w/w dispersion (right). This figure illustrates the crystallization-inducing potential of mannitol.

FIG. 3 shows DSC scan of in-situ generated amorphous celecoxib (left) and amorphous celecoxib and stearic acid physical mixture 50:50 w/w dispersion (right). This figure illustrates the crystallization-inducing potential of stearic acid.

FIG. 4 shows DSC scan of in-situ generated amorphous celecoxib (left) and amorphous celecoxib and cetostearyl alcohol physical mixture 50:50 w/w dispersion (right). This figure illustrates the crystallization-inducing potential of cetostearyl alcohol.

FIG. 5 shows DSC scan of in-situ generated amorphous celecoxib (left) and amorphous celecoxib and amorphous sorbitol physical mixture 50:50 w/w dispersion (right). This figure illustrates the crystallization-inducing potential of cetostearyl alcohol.

FIG. 6 shows DSC scan of in-situ generated amorphous celecoxib (left) and amorphous celecoxib and crystalline potassium chloride physical mixture 50:50 w/w dispersion (right). This figure illustrates the crystallization-inducing potential of potassium chloride.

FIG. 7 shows DSC scan of in-situ generated amorphous celecoxib (left) and amorphous celecoxib urea 75:25 w/w dispersion (right). This figure illustrates the plasticization effect of urea.

FIG. 8 shows DSC scan of celecoxib mannitol 50:50 w/w dispersion. This figure illustrates the crystalline nature of celecoxib in the dispersion (absence of Tg).

FIG. 9 shows DSC scan of celecoxib stearic acid 50:50 w/w dispersion. This figure illustrates the crystalline nature of celecoxib in the dispersion (absence of Tg).

FIG. 10 shows representative broadening of PXRD peaks of celecoxib in celecoxib stearic acid dispersion. This figure illustrates the smaller crystallite size of celecoxib in the dispersion compared to micron-sized crystalline celecoxib.

FIG. 11 shows representative broadening of PXRD peaks of aceclofenac in aceclofenac potassium chloride dispersion. This figure illustrates the smaller crystallite size of aceclofenac in the dispersion compared to micron-sized crystalline aceclofenac.

FIG. 12 shows representative broadening of PXRD peaks of Ibuprofen in ibuprofen mannitol dispersion. This figure illustrates the smaller crystallite size of ibuprofen in the dispersion compared to micron-sized crystalline ibuprofen.

FIG. 13 shows DSC scan of aceclofenac stearic acid dispersion 50:50 w/w. This figure illustrates the crystalline nature of celecoxib in the dispersion.

FIG. 14 shows PXRD of hesperetin and its nanocrystalline solid dispersion with mannitol in 50:50 w/w proportions; insect depicts measurement of peak width at half height.

FIG. 15 shows PXRD of naringenin and its nanocrystalline solid dispersion with mannitol in 50:50 w/w proportions; insect depicts measurement of peak width at half height.

FIG. 16 shows DSC scan of indomethacin:mannitol 50:50 w/w dispersion. Recrystallization and melting is evident for amorphous indomethacin in the presence of mannitol. Melting of mannitol is also visible.

FIG. 17 shows PXRD of indomethacin and its nanocrystalline solid dispersion with mannitol in 50:50 w/w proportions.

FIG. 18 Representative broadening of PXRD peaks of curcumin in curcumin:mannitol dispersion.

FIG. 19 shows PXRD overlay of Accelerated stability (40° C./75% RH) samples of Celecoxib Stearic acid 50:50% w/w nanocrystalline solid dispersion. This figure illustrates the physical form stability and unaffected crystallite size.

FIG. 20 shows PXRD overlay of Accelerated stability (40° C./75% RH) samples of Aceclofenac Potassium Chloride 50:50% w/w nanocrystalline solid dispersion. This figure illustrates the physical form stability and unaffected crystallite size.

FIG. 21 shows PXRD overlay of Accelerated stability (40° C./75% RH) samples of ibuprofen mannitol 50:50% w/w nanocrystalline solid dispersion. This figure illustrates the physical form stability and unaffected crystallite size.

FIG. 22 shows Mean plasma concentration-time profile of hesperetin mannitol physical mixture (HRN-M-PM) and hesperetin mannitol nanocrystalline solid dispersion (HRN-M)

FIG. 23 shows Mean plasma concentration-time profile of control (◊) and Curcumin stearic acid NSD (CRM-SA) (□)

FIG. 24 shows Mean plasma concentration-time profile of celecoxib mannitol physical mixture (CLB-M-PM) and their nanocrystalline solid dispersion (CLB-M)

Table 1 tabulates spray drying parameters for preparation of celecoxib:mannitol 50:50 w/w dispersion.

Table 2 tabulates spray drying parameters for preparation of celecoxib:stearic acid 50:50 w/w dispersion.

Table 3 tabulates spray drying parameters for preparation of aceclofenac:potassium chloride dispersion 50:50 w/w.

Table 4 tabulates dissolution profiles of aceclofenac:potassium chloride physical mixture and aceclofenac:potassium chloride dispersion in 50:50 w/w.

Table 5 tabulates spray drying parameters for preparation of nateglinide:potassium chloride dispersion 50:50 w/w.

Table 6 tabulates dissolution profiles of nateglinide:potassium chloride physical mixture and nateglinide potassium chloride dispersion in 50:50 w/w.

Table 7 tabulates spray drying parameters for preparation of ibuprofen:mannitol dispersion 50:50 w/w.

Table 8 tabulates dissolution profiles of ibuprofen:mannitol physical mixture and ibuprofen:mannitol dispersion in 50:50 w/w.

Table 9 tabulates spray drying parameters for preparation of aceclofenac:stearic acid dispersion 50:50 w/w.

Table 10 tabulates spray drying parameters for preparation of hesperetin:mannitol dispersion 50:50 w/w Table 11 tabulates dissolution profiles of hesperetin powder and hesperetin:mannitol dispersion in 50:50 w/w Table 12 tabulates spray drying parameters for preparation of naringenin:mannitol dispersion 50:50 w/w Table 13 tabulates dissolution profiles of naringenin:mannitol physical mixture and naringenin:mannitol dispersion in 50:50 w/w Table 14 tabulates spray drying parameters for preparation of indomethacin:mannitol 50:50 w/w dispersion Table 15 tabulates spray drying parameters for preparation of Curcumin:Mannitol 2:1 w/w dispersion Table 16 tabulates spray drying parameters for preparation of Curcumin:Stearic acid 50:50 w/w dispersion Table 17 tabulates dissolution profiles of curcumin:stearic acid physical mixture and curcumin:stearic acid dispersion 50:50 w/w Table 18 tabulates crystallite size of celecoxib in nanocrystalline solid dispersion during stability studies.

Table 19 tabulates crystallite size of aceclofenac in nanocrystalline solid dispersion during stability studies.

Table 20 tabulates dissolution profiles of aceclofenac:potassium chloride physical mixture and aceclofenac:potassium chloride dispersion in 50:50 w/w.

Table 21 tabulates dissolution profiles of Nateglinide:potassium chloride physical mixture and Nateglinide:potassium chloride dispersion in 50:50 w/w.

Table 22 tabulates crystallite size of Ibuprofen in nanocrystalline solid dispersion during stability studies.

Table 23 tabulates dissolution profiles of Ibuprofen:Mannitol physical mixture and Ibuprofen Mannitol Dispersion in 50:50 w/w.

Table 24 tabulates pharmacokinetic parameters of hesperetin observed after administration of HRN-M and HRN-M-PM after single oral dose (80 mg $kg^{-1}$) to male SD rats (n=5)

Table 25 tabulates pharmacokinetic parameters of curcumin observed after administration of control and CRM-SA after single oral dose (250 mg $kg^{-1}$) to female SD rats (n=5)

Table 26 tabulates pharmacokinetic parameters of celecoxib observed after administration of CLB-M and CLB-M-PM after single oral dose (5 mg $kg^{-1}$) to female SD rats (n=5)

DETAILED DESCRIPTION OF THE INVENTION

The present invention relates to novel one-step process for the preparation of compositions comprising nanocrystalline solid dispersions and compositions comprising nanocrystalline solid dispersions. The invention focuses on the process to make compositions containing hydrophobic pharmaceutical active and a hydrophilic crystallization inducer, exhibiting dissolution rate enhancement of hydrophobic pharmaceutical active. However, the present invention may find use for preparing a variety of other compositions comprising a variety of hydrophobic and hydrophilic components at different concentration ranges, including hydrophilic pharmaceutical active and hydrophobic crystallization-inducing excipients also including compositions having hydrophilic pharmaceutical active and crystallization-inducing excipient and compositions intended for non-pharmaceutical applications. The present invention will also relate to compositions containing either more than one pharmaceutical active or more than one crystallization-inducing excipient or both. The methods rely on spray drying liquid media in which the components, pharmaceutical active drug/s and crystallization-inducing excipient/s, of the composition are solubilized. The liquid media can be a suitable solvent or solvent mixture or solvent-water mixture. In particular, the hydrophobic and water-soluble crystallization-inducing excipient are solubilized in separate liquid media and mixed later. The solvent mixture is then spray dried. In case where both the components of the composition are hydrophobic, they can be dissolved in a common solvent and then spray dried. Final product is composed of fine discrete micron-sized particle and each discrete particle is composed of crystals of the components, hydrophobic drug and crystallization-inducing excipient, of the composition. The spray drying methods of the present invention were optimized to generate nanocrystalline hydrophobic drugs like Celecoxib, Nateglinide, Aceclofenac and Ibuprofen. This method is also suitable for crystallization-inducing excipient, non-limiting examples of which are mannitol, stearic acid, D-fructose and inorganic salts like potassium chloride. The spray drying methods can produce a homogeneous composition with uniform particle size distribution. The particles of the powders so produced have a minimum batch-to-batch variability in composition, and are physically and chemically stable.

In the process of the present invention for preparing pharmaceutical compositions the pharmaceutical active is usually present in the range of 0.01% to 95% of the powder, and the crystallization-inducing excipient, usually present in the range of 99.99% to 5% of the powder and is useful for enhancing the biopharmaceutical performance of hydrophobic pharmaceutical active. In particular, the process of the present invention comprises dissolving crystallization-inducing excipient in an organic solvent or co-solvent system. The pharmaceutical active is dissolved in the same organic solvent or co-solvent system to produce a solution. The organic solvent solution or co-solvent system is then spray dried to form particles comprising a mixture of the crystallization-inducing excipient and pharmaceutical active. Spray drying of pharmaceutical active-crystallization-inducing excipients solution would yield discrete particles in the micron-size range. Size of the particles is predominantly in the range of 0.5 to 20 micron, preferably in the range of 1 to 10 micron more preferably in the range of 2-8 micron. Each discrete particle of the composition is comprised of crystals of pharmaceutical active dispersed in matrix of crystallization-inducing excipients or coexisting with crystals of crystallization-inducing excipient. The size of the crystals of pharmaceutical active is in the range of 10-2000 nm. The organic solvent or solvent mixture is selected to provide a solubility of the components, crystallization-inducing excipient and pharmaceutical active, of the composition. Suitable organic solvents or solvent systems are selected to provide additional characteristics, like complete evaporation at the optimized spray drying conditions. A presently preferred co-solvent system comprise of water: methanol at a weight ratio in the range from 90:10 to 10:90, usually from 30:70 to 20:80, preferably 25:75, when water-soluble crystallization excipients like polyols, sugars, are used. However, solvent system can compose of only methanol when hydrophobic crystallization-inducing excipients like stearic acid are used. The solvents which can be used for dissolving the components of the composition can be selected from the group consisting of acetic acid, acetonitrile, acetone, 1-butanol, 2-butanol, N,N-dimethyl-acetamide; N,N-dimethylformamide, dimethyl sulfoxide, 1,4-dioxane, ethanol, formic acid, methanol, 3-methyl-1-butanol, methylethyl ketone, 2-methyl-1-propanol, 1-methyl-2-pyrrolidone, 1-pentanol, 1-propanol, 2-propanol and tetrahydrofuran.

Powder prepared by the above process will be collected from the spray drier in a conventional manner for subsequent use. For further use, it will be desirable to disrupt any agglomerates which may have formed during spray drying by screening or other conventional techniques.

Additional pharmaceutical excipients can be included to enhance the functionality, processing or stability of the pharmaceutical active. Of special interest are solubilizers, pH-modifying agents, surfactants and desiccating agents. This pharmaceutical composition can further be formulated in to a dosage form.

The present invention is novel and inventive in the use of selected excipients to induce crystallization of the drug and optimized process parameters to generate nanocrystalline solid dispersions. Process parameters are optimized in such a way that both the components of the composition are crystallized. This inventive step ensures one-step process of generating nanocrystalline solid dispersion and also physical stability, as both the components are in crystalline form.

Unless defined otherwise, technical and scientific terms used herein have the same meaning as commonly understood by one of ordinary skill in the art to which this invention belongs. Some of the terms are defined briefly herebelow; the definitions should not be construed in a limiting sense.

Description/Definition of the Terms Used in the Application:

The terminology used herein is for the purpose of describing particular embodiments only and is not intended to be limiting.

The term pharmaceutical active refers to the compounds which have therapeutic activity. A pharmaceutical active can be hydrophilic or hydrophobic based on its molecular structure. The term "hydrophobic pharmaceutical active" refers to materials which have either dissolution-limited absorption or solubility-limited dissolution or both dissolution and solubility-limited absorption. Hydrophobic drug is said to exhibit "dissolution-limited absorption" when the dissolution time of hydrophobic drug is greater than mean intestinal transit time. "Dissolution time" is defined as the time required for the complete dissolution of a single particle under sink conditions. Hydrophobic drug is said to exhibit "solubility-limited dissolution" when absorbable dose is lesser than the intended dose. "Absorbable dose" is defined as amount of drug that can be absorbed during period of transit time when solution contacting the effective intestinal surface area of absorption is saturated with the drug. The phrase "hydrophobic pharmaceutical active" and "hydrophobic drug" is used interchangeably. Exemplary hydrophobic drugs that can be used in accordance with the present invention include, but are not limited to, hydrophobic drug or a salt, isomer, ester, ether or other derivative thereof selected from:

(i) acetylcholinesterase inhibitors selected from donepezil, tacrine, pyridostigmine;

(ii) analgesics and nonsteroidal anti-inflammatory agents (NSAIA) selected from aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, oxaprozin, oxyphenbutazone, phenylbutazone, piroxicam, rofecoxib, sulindac, tetrahydrocannabinol, tramadol and tromethamine, (iii) anthelminthics selected from albendazole, bephenium hydroxynaphthoate, cambendazole, dichlorophen, fenbendazole, ivermectin, mebendazole, oxamniquine, oxfendazole, oxantel embonate, praziquantel, pyrantel embonate and thiabendazole;

(iv) antiacne agents such as isotretinoin and tretinoin;

(iv) antianginal agents selected from amyl nitrate, glyceryl trinitrate (nitroglycerin), isosorbide dinitrate, isosorbide mononitrate, pentaerythritol tetranitrate, and ubidecarenone (coenzyme Q10);

(v) antiarrhythmic agents selected from amiodarone HCl, digoxin, disopyramide, flecamide acetate and quinidine sulfate;

(vi) anti-asthma agents selected from zileuton, zafirlukast, terbutaline sulfate, montelukast, and albuterol;

(vii) antibacterial agents, including antibiotics, selected from alatrofloxacin, azithromycin, aztreonum, baclofen, benzathine penicillin, cefixime, cefuraxime axetil, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, phenoxymethyl penicillin, rifabutine, rifampicin, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin;

(vii) anti-benign prostate hypertrophy (BPH) agents selected from alfuzosin, doxazosin, phenoxybenzamine, prazosin, terazosin and tamulosin;

(viii) anticancer agents and immunosuppressants selected from abarelix, aldesleukin, alemtuzumab, alitretinoin, all-trans retinoic acid (ATRA), altretamine, amifostine, aminoglutethimide, amsacrine, anastrozole, arsenic trioxide, asparaginase, azacitidine, azathioprine, BCG Live, bevacuzimab (avastin), bexarotene, bicalutamide, bisantrene, bleomycin, bortezomib, busulfan, calusterone, camptothecin, capecitabine, carboplatin, carmustine, celecoxib, cetuximab, chlorambucil, cisplatin, cladribine, clofarabine, cyclophosphamide, cyclosporin, cytarabine, dacarbazine, dactinomycin, darbepoetin alfa, daunorubicin, denileukin, dexrazoxane, docetaxel, doxorubicin (neutral), doxorubicin HCl, dromostanolone propionate, ellipticine, enlimomab, estramustine, epirubicin, epoetin alfa, erlotinib, estramustine, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, mesna, methotrexate, methoxsalen, mitomycin C, mitotane, mitoxantrone, mofetil mycophenolate, nandrolone, nelarabine, nilutamide, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sirolimus, sorafenib, streptozocin, sunitinib maleate, tacrolimus, tamoxifen citrate, temozolomide, teniposide, testolactone, thioguanine, thiotepa, topotecan, toremifene, tositumomab, trastuzumab, tretinoin, uracil mustard, valrubicin, vinblastine, vincristine, vinorelbine, zoledronate, and zoledronic acid;

(ix) anticoagulants selected from cilostazol, clopidogrel, dicumarol, dipyridamole, nicoumalone, oprelvekin, phenindione, ticlopidine, and tirofiban;

(x) antidepressants selected from amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl;

(xi) antidiabetics selected from acetohexamide, chlorpropamide, glibenclamide, gliclazide, glipizide, glimepiride, glyburide, miglitol, pioglitazone, repaglinide, rosiglitazone, tolazamide, tolbutamide and troglitazone;

(xii) antiepileptics selected from beclamide, carbamazepine, clonazepam, thotoin, felbamate, fosphenyloin sodium, lamotrigine, methoin, methsuximide, methylphenobarbitone, oxcarbazepine, paramethadione, phenacemide, phenol barbitone, phenyloin, phensuximide, primidone, sulthiame, tiagabine HCl, topiramate, valproic acid, and vigabatrin;

(xiii) antifungal agents selected from amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid;

(xiv) antigout agents selected from allopurinol, probenecid and sulphinpyrazone;

(xv) antihypertensive agents selected from amlodipine, benidipine, benezepril, candesartan, captopril, darodipine, dilitazem HCl, diazoxide, doxazosin HCl, enalapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan;

(xvi) antimalarial agents selected from amodiaquine, chloroquine, chlorproguanil HCl, halofantrine HCl, mefloquine HCl, proguanil HCl, pyrimethamine and quinine sulfate;

(xvii) antimigraine agents selected from dihydroergotamine mesylate, ergotamine tartrate, frovatriptan, methysergide maleate, naratriptan HCl, pizotifen maleate, rizatriptan benzoate, sumatriptan succinate, and zolmitriptan;

(xviii) antimuscarinic agents selected from atropine, benzhexol HCl, biperiden, ethopropazine HCl, hyoscyamine, mepenzolate bromide, oxyphencyclimine HCl and tropic amide (xix) antiparkinsonian agents selected from bromocriptine mesylate, lysuride maleate, pramipexole, ropinirole HCl, and tolcapone;

(xx) antiprotozoal agents selected from atovaquone, benznidazole, clioquinol, decoquinate, diiodohydroxyquinoline, diloxamide furoate, dinitolmide, furazolidone, metronidazole, nimorazole, nitrofurazone, ornidazole and tinidazole;

(xxi) antithyroid agents selected from carbimazole and propylthiouracil;

(xxii) antitussive agent such as benzonatate;

(xxiii) antiviral agents selected from abacavir, amprenavir, delavirdine, efavirenz, indinavir, lamivudine, nelfinavir, nevirapine, ritonavir, saquinavir, and stavudine;

(xxiv) anxiolytics, sedatives, hypnotics and neuroleptics selected from alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, flupenthixol decanoate, fluphenthixol decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, propofol, pseudoephedrine, quetiapine, risperidone, sertindole, sulpiride, temazepam, thioridazine, triazolam, zolpidem, and zopiclone;

(xxv) beta.-blockers selected from acebutolol, alprenolol, atenolol, labetalol, metoprolol, nadolol, oxprenolol, pindolol and propranolol;

(xxvi) cardiac inotropic agents selected from anrinone, digitoxin, digoxin, enoximone, lanatoside C and medigoxin;

(xxvii) corticosteroids selected from beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone;

(xxviii) diuretics selected from acetazolamide, amiloride, bendroflumethiazide, bumetanide, chlorothiazide, chlorthalidone, ethacrynic acid, frusemide, metolazone, spironolactone and triamterene;

(xxix) gastrointestinal agents selected from bisacodyl, cimetidine, cisapride, diphenoxylate HCl, domperidone, famotidine, lanosprazole, loperamide, mesalazine, nizatidine, omeprazole, ondansetron HCl, pantoprazole, rabeprazole sodium, ranitidine HCl and sulphasalazine;

(xxx) histamine $H_1$- and $H_2$-receptor antagonists selected from acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine;

(xxxi) keratolytic agents selected from acetretin, calcipotriene, calcifediol, calcitriol, cholecalciferol, ergocalciferol, etretinate, retinoids, targretin, and tazarotene;

(xxxii) lipid regulating/hypolipidemic agents selected from atorvastatin, bezafibrate, cerivastatin, ciprofibrate, clofibrate, fenofibrate, fluvastatin, gemfibrozil, hesperetin, lovastatin, pravastatin, probucol, and simvastatin;

(xxxiv) muscle relaxants selected from cyclobenzaprine, dantrolene sodium and tizanidine HCl;

(xxxv) opioid analgesics selected from codeine, dextropropoxyphene, diamorphine, dihydrocodeine, fentanyl, meptazinol, methadone, morphine, nalbuphine and pentazocine;

(xxxvi) sex hormones selected from clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, mifepristone, norethisterone, norgestrel, oestradiol, conjugated estrogens, progesterone, rimexolone, stanozolol, stilbestrol, testosterone and tibolone;

(xxxvii) stimulants selected from amphetamine, dexamphetamine, dexfenfluramine, fenfluramine and mazindol;

Preferred hydrophobic drugs used in the present invention are the drugs celecoxib, nateglinide, aceclofenac, ibuprofen and curcumin The term "Veterinary active" refers to the compounds which have therapeutic activity in animals. Exemplary Veterinary active that can be used in accordance with the present invention include, but are not limited to albendazole, fenbendazole and itraconazole.

The term "Nutraceutical active" refers to the food or food product that reportedly provides health and medical benefits, including the prevention and treatment of disease. Exemplary Nutraceutical agents that can be used in accordance with the present invention include, but are not limited to calcitriol, carotenes, chrysin, dihydrotachysterol, flavonoids, hesperitin, jasmonates, lipoic acid, lutein, lycopene, essential fatty acids, non-essential fatty acids, naringenin, phytonadiol, quercetin, vitamins including vitamin A, vitamin B2, vitamin D and derivatives, vitamin E, and vitamin K, coenzyme Q10 (ubiquinone), plant extracts, and minerals.

By "crystallization-inducing excipient", it is meant that the component is a pharmaceutical inactive which induces the crystallization of the pharmaceutical active. The "crystallization-inducing excipients" and "crystallization inducers" is used interchangeably. The excipients are generally selected to provide crystallizing environment to the pharmaceutical active in the spray drying conditions. The crystallization-inducing excipient influences multiple events to produce nanocrystalline active agent. The selected crystallization inducer should be such that, in its presence, active agent's crystallization temperature should decrease significantly. Crystals of crystallization inducer grow in the vicinity of the pharmaceutical active agent, thus limiting the crystal size of active agent in the desired range. For example, in-situ generated amorphous celecoxib does not crystallize in the subsequent heating run in DSC, however, in the presence of mannitol, the crystallization temperature of celecoxib decreases to around 90° C. Same phenomenon is observed in the presence of stearic acid as crystallization-inducing excipient. These crystallization-inducing excipients have a different role when drug itself crystallizes fast (i.e. crystallizing in the subsequent heating run after in-situ generation). For example, nateglinide crystallizes in the subsequent heating run after initial in-situ generation. Crystallization-inducing excipients, besides increasing the probability of crystallization of the pharmaceutical active, physically place themselves between the crystals of the pharmaceutical active and inhibit the crystal growth.

Crystallization-inducing excipient has a glass transition temperature (Tg) value lesser than the active agent and crystallizes during the spray drying process. Crystallization-inducing excipients also include those excipients which decrease the Tg of the pharmaceutical active. For example, in-situ generated amorphous celecoxib has Tg around 55-60° C. However, in the presence of 25% w/w of urea, the Tg of dispersion decreases to 29-35° C. The decrease of Tg of pharmaceutical active will also increase the probability of crystallization indirectly, which is well documented in literature dealing with amorphous systems. Crystallization of pharmaceutical active is very important for the physical stability of the formulation. These crystallization-inducing excipients play a major role to induce crystallization. It is well known that lower molecular weight, lower Tg, lower crystallization temperature and lower melting point are responsible for easier crystallization.

Apart from the criteria of Tg value lesser than active agent, the crystallization-inducing excipient provides heterogeneous nucleation site and induces crystallization of the active agent during the spray drying process. Heterogeneous nucleation is the spontaneous formation of nuclei of active agent on the solid particles of crystallization-inducing excipient. Crystallization of the active agent is thus facilitated. This gets reflected as a decrease in recrystallization temperature (Tc) of the active agent.

It is also important that the crystallization-inducing excipient possesses relatively fast crystallization kinetics in comparison to the active agent so as to act as crystallization inducer for the active agent. For example, mannitol though has a higher Tg as compared to fructose, acts as an efficient crystallization inducer because of faster crystallization kinetics. D-fructose despite its low Tg is not able to induce crystallization because of its slow crystallization kinetics.

Another important property of crystallization-inducing excipients is its miscibility with active agent. This manifests in various ways, to enable crystallization of the API. Miscibility of the excipient with the active agent, may reduce Tg, and encourage crystallization. Immiscible excipient may provide heterogeneous nucleation sites for active agent to crystallize. Viscosity of the crystallization inducer has also had profound influence on its potential to generate nanocrystalline active. As the higher viscosity has a negative effect on crystallization, preferably crystallization-inducing excipients should have less viscosity.

The selection of spray drying process parameters is also crucial for successful formation of nanocrystalline active agent. Preferably the drying temperature should be higher than Tg of the API, observed in presence of crystallization inducer. A combination of drying temperature and aspirator flow rate plays important role in successful formation of nanocrystalline solid dispersion of the active agent. An optimal value of temperature, as guided by Tg and Tc observed for mixture of drug and excipient in DSC analysis, combined with optimal residence time provides suitable residence time, thus providing suitable conditions for formation of nanocrystals.

From classical view of the crystallization process in glass forming systems, nucleation is thermodynamically favored at lower temperatures and crystal growth is favored at higher temperatures. Thus, drying temperature in vicinity of Tg encourages nucleation. However, heterogeneous nucleation contributed by the crystallization inducing excipient also plays a critical role.

Pharmaceutical excipients that are non-polymeric in nature serve this purpose of inducing crystallization. Pharmaceutical excipients that are crystalline with low molar mass and low melting point are found to be effective for this purpose. Though few pharmaceutical excipients have very high melting point, but because of their low molecular weight their crystallization tendency is very high. For example, potassium chloride, sodium chloride etc. Pharmaceutical excipients that have lower glass transition temperature, particularly, lesser than that of drug or spray drying condition, would also be appropriate for inducing crystallization. Examples of crystallization inducing excipients may include, but are not limited to, Acesulfame potassium, ascorbic acid, ascorbyl palmitate, aspartame, benzoic acid, butyl paraben, calcium carbonate, calcium phosphate, calcium stearate, calcium sulphate, chlorbutanol, chlorocresol, citric acid, dextrose, ethyl maltol, fructose, fumaric acid, glyceryl monostearate, glycreyl palmitostearate, lactitol, lauric acid, magnesium carbonate, malic acid, malttitol, maltose, mannitol, meglumine, methyl paraben, palmitic acid, phenyl mercuric acetate, potassium chloride, potassium citrate, potassium sorbate, propyl gallate, propyl paraben, saccharin, saccharin sodium, sodium ascorbate, sodium benzoate, sodium bicarbonate, sodium chloride, sodium citrate, sodium cyclamate, sodium lauryl suphate, sodium metabisulfate, sodium phosphate, sodium propionate, sorbic acid, sorbitol, stearic acid, stearyl alcohol, sucrose, tartaric acid, xylitol and their hydrates and their salts. Particularly preferred crystallization inducers in the present invention are mannitol, stearic acid, palmitic acid, lauric acid, d-fructose and potassium chloride. The crystallization inducers in the composition may be water-soluble or may not be water-soluble. However, water-soluble crystallization-inducing excipients would increase the dissolution kinetics of hydrophobic pharmaceutical active used in the composition. Compositions having more than one hydrophobic drug or more than one crystallization inducers are also included in the present invention. The crystallization inducer may or may not act as solubilizer for the hydrophobic pharmaceutical active.

The term "crystal" is a solid material whose constituent atoms, molecules, or ions are arranged in an orderly repeating pattern extending in all three spatial dimensions. Crystals can vary in size from a few nanometers to several millimeters. The term "crystal" is used in the present invention for describing the nature of pharmaceutical active and/or crystallization inducing excipients in the composition. As the size of crystals is determined by powder X-ray diffraction, terms "crystallite and "crystal" can be used interchangeably. These crystals can exist solitary or in agglomerates, i.e the discrete particles of dispersion, may comprise of crystal-level coexistence of pharmaceutical active and crystallization inducing excipients or agglomerates of pharmaceutical active crystallites coexisting with agglomerates of crystallites of crystallization-inducing excipients. Average crystallite size of drug crystallites was calculated based on PXRD peak broadening using the Scherrer equation—

$$\tau = \frac{K\lambda}{\beta_\tau \cos\theta}$$

where τ is the mean crystallite dimension, K is a constant of 0.9, λ is the X-ray wavelength (1.542 nm), $\beta_\tau$ is the line broadening value due to crystal size reduction, i.e., the full-width-at-half-maximal (FWHM) difference in radian at a certain Bragg angle (Θ), between a nanocrystalline sample and the micron-sized drug crystals.

Drying of pharmaceutical active-crystallization-inducing excipients can be done using any conventional method for drying solutions such as, but not limited to, spray drying, and evaporation by heating under vacuum. In the method of the invention, when the solution of crystallization inducer-hydrophobic drug is dried, the drying conditions were optimized in such a way that pharmaceutical active in the composition is primarily present as crystalline. For example, to prepare a composition containing celecoxib and mannitol, the above components should be dissolved in suitable solvent or solvent mixture and dried using spray drying. The spray drying parameters like inlet temperature/outlet temperature, feed rate, atomization pressure are optimized to allow the crystallization of the components. Precisely, crystallization temperatures of the pharmaceutical active and crystallization inducer should be known individually and in the mixture. Crystallization temperature of components can be assessed by Differential Scanning calorimeter (DSC). In-situ prepared amorphous dispersions, by melt quenching, can be heated at a constant rate to know the crystallization temperature of the components. This information is used in defining the spray dryer conditions. The dried powder is subjected to this temperature by altering the spray drying parameters like inlet/outlet temperature, atomization pressure, vacuum and mode of spray (co-current/counter-current).

The phrase "discrete micron-sized particles" means a powder composition comprising a plurality of discrete, dry particles having the characteristics set forth below. In particular, the dry particles will have an average particle size in micron-range. The average particle size of the powder will be measured as $d_{50}$ or $d_{90}$ by conventional techniques. A particular powder sizing technique uses a pre-calibrated stage micrometer using optical microscope. The powders will be capable of being readily used for further formulation development.

The crystallization inducer in the composition ensures crystallization of drug in nano-range, by placing itself physically between the crystals. As a result, drug in the composition ends up in nanoscale level. And when this composition comes in contact with dissolution media, the crystallization-inducing excipients, if it is water-soluble, gets dissolved thus presenting the hydrophobic drug in the nanoscale to the dissolution media, thus enhancing the dissolution kinetics of hydrophobic drug due to higher surface area.

As mentioned above, pharmaceutical active is, predominantly, crystalline in nature in the final product. The interaction between pharmaceutical active and crystallization inducer in the composition is limited to sub-particle level. The crystals of the pharmaceutical active were physically separated by crystals of crystallization inducer used in the composition without any interaction, thus physico-chemical properties of the pharmaceutical active remain unaltered.

When the composition of the invention, particularly of hydrophobic pharmaceutical active and water-soluble crystallization inducer, come in contact with dissolution medium, especially aqueous media, the crystals of water-soluble excipients are easily dissolved thus ensuring nanocrystalline of pharmaceutical active in the dissolution media. This process ensures higher surface area of pharmaceutical active thus enhancing its dissolution kinetics.

The nanocrystalline solid dispersion composition of invention is stable against the crystal growth and chemical degradation. Crystal growth would be arrested as crystallization inducer would place physically between the crystals of hydrophobic drug. Physical and chemical stability of the pharmaceutical active is ensured because, the pharmaceutical active would be present in the crystalline state and as it is crystalline, the interaction between pharmaceutical active and crystallization inducer would be minimal thus stability would be maximum.

In one aspect of the invention, a nanocrystalline solid dispersion composition having discrete particles, wherein each discrete particle comprises crystals of at least one pharmaceutical active; veterinary active; nutraceutical active dispersed in the matrix of at least one crystallization inducer and/or coexisting with crystals of crystallization inducer, optionally along with pharmaceutically acceptable excipients.

Another aspect of the invention provides the nanocrystalline solid dispersion composition in powder form.

Yet another aspect of the invention provides the nanocrystalline solid dispersion composition, wherein pharmaceutical active; veterinary active; nutraceutical active is present in the range of 0.01% to 95% of the powder, and the crystallization inducer, is present in the range of 99.99% to 5% of the powder.

Yet another aspect of the invention provides the nanocrystalline solid dispersion composition, wherein each discrete particle has the pharmaceutical active; veterinary active; nutraceutical active crystals in a range of 10 to 1000 nm.

Yet another aspect of the invention provides the nanocrystalline solid dispersion composition, wherein at least about 90% of the discrete particles have the average particle size in the range of 0.5 to 20 micron, preferably in the range of 2 to 8 micron.

Yet another aspect of the invention provides the nanocrystalline solid dispersion composition, wherein the pharmaceutical active is selected from hydrophilic or hydrophobic pharmaceutical active.

Yet another aspect of the invention provides the nanocrystalline solid dispersion composition, wherein said pharmaceutical active is hydrophobic pharmaceutical active having either dissolution-limited or solubility-limited or solubility and dissolution-limited absorption.

Yet another aspect of the invention provides the nanocrystalline solid dispersion composition, wherein said pharmaceutical active is selected from the group comprising acetylcholinesterase inhibitors, analgesics and nonsteroidal anti-inflammatory agents (NSAIDs), antihelminthics, anti-acne agents, antianginal agents, antiarrhythmic agents, anti-asthma agents, antibacterial agents, anti-benign prostate hypertrophy (BPH) agents, anticancer agents and immunosuppressants, anticoagulants, antidepressants, antidiabetics, antiepileptics, antifungal agents, antigout agents, antihypertensive agents, antimalarial agents, antimigraine agents, antimuscarinic agents, antiparkinsonian agents, antiprotozoal agents, antithyroid agents, antitussive agent, antiviral agents, anxiolytics, sedatives, hypnotics and neuroleptics, beta.-blockers, cardiac inotropic agents, corticosteroids, diuretics, gastrointestinal agents, histamine H1- and H2-receptor antagonists, keratolytic agents, lipid regulating/hypolipidemic agents, muscle relaxants, opioid analgesics, sex hormones, stimulants.

Yet another aspect of the invention provides the nanocrystalline solid dispersion composition, wherein said pharmaceutical active is preferably celecoxib, aceclofenac, nateglinide, ibuprofen and curcumin.

Yet another aspect of the invention provides the nanocrystalline solid dispersion composition, wherein said veterinary active is selected from the group comprising albendazole, fenbendazole and itraconazole.

Yet another aspect of the invention provides the nanocrystalline solid dispersion composition, wherein said nutraceutical active is selected from the group comprising calcitriol, carotenes, chrysin, dihydrotachysterol, flavonoids, hesperitin, jasmonates, lipoic acid, lutein, lycopene, essential fatty acids, non-essential fatty acids, naringenin, phytonadiol, quercetin, vitamins including vitamin A, vitamin B2, vitamin D and derivatives, vitamin E, and vitamin K, coenzyme Q10 (ubiquinone), plant extracts, and minerals.

Yet another aspect of the invention provides the nanocrystalline solid dispersion composition, wherein said nutraceutical active is preferably resveratrol or hesperetin or naringenin Yet another aspect of the invention provides the nanocrystalline solid dispersion composition, wherein the said crystallization inducer is selected from the group comprising acesulfame potassium, ascorbic acid, ascorbyl palmitate, aspartame, benzoic acid, butyl paraben, calcium carbonate, calcium phosphate, calcium stearate, calcium sulphate, Cetosteary alcohol, chlorbutanol, chlorocresol, citric acid, d-fructose dextrose, ethyl maltol, fructose, fumaric acid, glyceryl monostearate, glycreyl palmitostearate, lactitol, lauric acid, magnesium carbonate, malic acid, malttitol, maltose, mannitol, meglumine, methyl paraben, palmitic acid, phenyl mercuric acetate, potassium chloride, potassium citrate, potassium sorbate, propyl gallate, propyl paraben, saccharin, saccharin sodium, sodium ascorbate, sodium benzoate, sodium bicarbonate, sodium chloride, sodium citrate, sodium cyclamate, sodium lauryl suphate, sodium metabisulfate, sodium phosphate, sodium propionate, sorbic acid, sorbitol, stearic acid, stearyl alcohol, sucrose, tartaric acid, urea, xylitol, salts and hydrates thereof.

Yet another aspect of the invention provides the nanocrystalline solid dispersion composition, wherein said crystallization inducer is preferably mannitol, stearic acid, Cetosteary alcohol, sorbitol, potassium chloride, urea, salts and hydrates thereof.

Yet another aspect of the invention provides the nanocrystalline solid dispersion composition, wherein the composition comprises of spray dried particles.

Yet another aspect of the invention provides the nanocrystalline solid dispersion composition, wherein said pharmaceutical active is a non-steroidal anti-inflammatory drug (NSAID) or anti-diabetic drug selected from Celecoxib, Nateglinide, Aceclofenac and Ibuprofen and crystallization-inducer excipient is a polyol or a saturated fatty acid or an inorganic salt selected from mannitol, sorbitol, stearic acid and potassium chloride.)

Yet another aspect of the invention provides the nanocrystalline solid dispersion composition, wherein said veterinary active preferably has albendazole, fenbendazole and itraconazole and crystallization-inducing excipient is a polyol or a saturated fatty acid or an inorganic salt.

Yet another aspect of the invention provides the nanocrystalline solid dispersion composition, wherein said nutraceutical active preferably has resveratrol or hesperetin or naringenin and crystallization-inducing excipient is a polyol or a saturated fatty acid.

Yet another aspect of the invention provides the nanocrystalline solid dispersion composition, which is designed for release of the pharmaceutical active either in the stomach or in the intestine, preferably a composition that has higher biopharmaceutical performance upon contact with biological fluids with pH 6-8 that corresponds to the pH of intestinal fluids.

Yet another aspect of the invention provides the nanocrystalline solid dispersion composition, which is stable against crystal growth of pharmaceutical active within shelf-life and does not exhibit any changes in the chemical or physicochemical properties, particularly exhibiting enhanced dissolution rate.

Yet another aspect of the invention provides the nanocrystalline solid dispersion composition, wherein said composition shows improved bioavailability compared to crude physical mixture.

Yet another aspect of the invention provides the nanocrystalline solid dispersion composition, wherein said composition provides a relative bioavailability that is at least 1.6-fold that of a control composition consisting essentially of an equivalent amount of crude physical mixture of said active and crystallization inducer.

Yet another aspect of the invention provides the nanocrystalline solid dispersion compositions, wherein said compositions provide an enhancement of relative bioavailability in the range of 1.6-15.2 fold.

Yet another aspect of the invention provides the nanocrystalline solid dispersion composition, wherein said pharmaceutically acceptable excipients are selected from solubilizers, pH modifying agents, surfactants and desiccating agents.

Yet another aspect of the invention provides a process for the preparation of a nanocrystalline solid dispersion composition, comprising the steps of:
(i) preparing a clear and homogeneous solution of crystallization-inducing excipient and the at least one pharmaceutical active compound in a mixture of water and an organic solvent or organic solvent alone; and
(ii) drying the crystallization-inducing excipients-pharmaceutical active clear and homogeneous solution as obtained in step (i) to form a dry powder.

Yet another aspect of the invention provides the process, wherein the drying in step (ii) is carried out by conventional drying techniques like spray drying, vacuum drying, solvent evaporation etc.

Yet another aspect of the invention provides the process wherein preferred drying technique is spray drying.

Yet another aspect of the invention provides the process, wherein the clear and homogeneous solution of crystallization-inducing excipients-pharmaceutical active solution is obtained by preparing a solution of the pharmaceutical active in an organic solvent, adding the clear solution of crystallization-inducing excipients in organic solvent or aqueous media or aqueous-solvent mixture to the pharmaceutical active organic solution.

Yet another aspect of the invention provides the process, wherein the organic solvent is selected from the group consisting of alcohols, ketones, ethers, aldehydes, hydrocarbons and polar aprotic solvents and mixtures thereof Yet another aspect of the invention provides a pharmaceutical or a veterinary or a nutritional, or nutraceutical product comprising the nanocrystalline solid dispersion composition.

Yet another aspect of the invention provides a nanocrystalline solid dispersion composition for use as a medicament for the treatment of disease state or condition selected from Inflammatory diseases, helminthic infections, acne, angina, arrhythmia, asthma, bacterial infections, benign prostate hypertrophy (BPH), cancer, depression, diabetes, epilepsy, fungal infections, gout, hypertension, malarial, migraine, Parkinsons Disease, protozoal infections, thyroid disorders, viral infections, diuretics, gastrointestinal disorders.

Yet another aspect of the invention provides a use of the nanocrystalline solid dispersion composition for the treatment of disease state or condition selected from Inflammatory diseases, helminthic infections, acne, angina, arrhythmia, asthma, bacterial infections, benign prostate hypertrophy (BPH), cancer, depression, diabetes, epilepsy, fungal infections, gout, hypertension, malarial, migraine, Parkinsons Disease, protozoal infections, thyroid disorders, viral infections, diuretics, gastrointestinal disorders.

Yet another aspect of the invention provides a method for the treatment of a disease state or condition in a patient in need thereof (e.g. a mammal such as a human), which method comprises administering to the said patient a therapeutically effective amount of a nanocrystalline solid dispersion composition, wherein the disease state or condition is selected from: Inflammatory diseases, helminthic infections, acne, angina, arrhythmia, asthma, bacterial infections, benign prostate hypertrophy (BPH), immune disorders, cancer, depression, diabetes, epilepsy, fungal infections, gout, hypertension, malarial, migraine, Parkinsons Disease, protozoal infections, thyroid disorders, viral infections, diuretics, gastrointestinal disorders.

It is another aspect of this invention, to include other pharmaceutical excipients like solubilizers, pH modifying agents, surfactants and desiccating agents in the product. Excipients like solubilizers, pH modifying agents and surfactants can help in enhancing stability of the product. Desiccating agents and glidants can help in improving the flow properties and thus processability of the product.

The present disclosure with reference to the accompanying examples describes the present invention. However, those of skill in the art should, in light of the present disclosure, appreciate that many changes can be made in the specific embodiments which are disclosed and still obtain a like or similar result without departing from the spirit and scope of the invention. It is understood that the examples are provided for the purpose of illustrating the invention only, and are not intended to limit the scope of the invention in any way.

EXAMPLES

Example 1: Celecoxib:Mannitol 50:50% w/w

In-Situ Generated Amorphous Celecoxib

Accurately weighed amount of celecoxib was heated to 180° C. to melt crystalline celecoxib completely. It was held at 180° C. for 2 min isothermally, and then cooled to 20° C. at 20° C./min ramp. The in-situ generated amorphous celecoxib was subsequently heated at 20° C./min to determine the crystallization temperature. However, it was observed that, in-situ generated amorphous celecoxib did not crystallize in the subsequent heating.

Crystallization of Celecoxib in the Presence of Mannitol

Accurately weighed amount of celecoxib and mannitol physical mixture in 50:50% w/w is heated to 180° C. to melt crystalline celecoxib completely, and held at 180° C. for 2 min isothermally, and then cooled to 20° C. at 20/min ramp. However, in the subsequent heating run it was observed the celecoxib crystallized around 120° C. This indicates that the presence of mannitol influences the crystallization of celecoxib. DSC scans of in situ generated amorphous celecoxib and celecoxib mannitol physical mixture in 50:50% w/w is presented in FIG. 2.

Example 2: Celecoxib:Stearic Acid 50:50% w/w

In-Situ Generated Amorphous Celecoxib

Accurately weighed amount of celecoxib was heated to 180° C. to melt crystalline celecoxib completely. It was held at 180° C. for 2 min isothermally, and then cooled to 20° C. at 20° C./min ramp. The in-situ generated amorphous celecoxib was subsequently heated at 20° C./min to determine the crystallization temperature. However, it was observed that, in-situ generated amorphous celecoxib did not crystallize in the subsequent heating.

Crystallization of Celecoxib in the Presence of Stearic Acid

Accurately weighed amount of celecoxib and stearic acid physical mixture in 50:50% w/w was heated to 180° C. to melt crystalline celecoxib completely, and held at 180° C. for 2 min isothermally, and then cooled to 20° C. at 20/min ramp. However, in the subsequent heating run it was observed the celecoxib had crystallized around 70° C. This indicates that the presence of stearic acid is influencing the crystallization of celecoxib. DSC scans of in situ generated amorphous celecoxib and celecoxib stearic acid physical mixture in 50:50% w/w is presented in FIG. 3.

Example 3: Celecoxib:Cetosteary Alcohol 50:50% w/w

In-Situ Generated Amorphous Celecoxib

Accurately weighed amount of celecoxib was heated to 180° C. to melt crystalline celecoxib completely. It was held at 180° C. for 2 min isothermally, and then cooled to 20° C. at 20° C./min ramp. The in-situ generated amorphous celecoxib was subsequently heated at 20° C./min to determine the crystallization temperature. However, it was observed that, in-situ generated amorphous celecoxib did not crystallize in the subsequent heating Crystallization of Celecoxib in the Presence of Cetostearyl Alcohol Accurately weighed amount of celecoxib and cetostearyl alcohol physical mixture in 50:50% w/w was heated to 180° C. to melt crystalline celecoxib completely, and held at 180° C. for 2 min isothermally, and then cooled to 20° C. at 20/min ramp. However, in the subsequent heating run it was observed the celecoxib crystallized around 65° C. This indicates that the presence of cetostearyl alcohol is also influencing the crystallization of celecoxib. DSC scans of in situ generated amorphous celecoxib and celecoxib:cetosteary alcohol physical mixture in 50:50% w/w is presented in FIG. 4.

Example 4: Celecoxib:Sorbitol 50:50% w/w

In-Situ Generated Amorphous Celecoxib

Accurately weighed amount of celecoxib was heated to 180° C. to melt crystalline celecoxib completely. It was held at 180° C. for 2 min isothermally, and then cooled to 20° C. at 20° C./min ramp. The in-situ generated amorphous celecoxib was subsequently heated at 20° C./min to determine the crystallization temperature. However, it was observed that, in-situ generated amorphous celecoxib did not crystallize in the subsequent heating Crystallization of Celecoxib in the Presence of Sorbitol Accurately weighed amount of celecoxib and sorbitol physical mixture in 50:50% w/w was heated to 180° C. to melt crystalline celecoxib completely, and held at 180° C. for 2 min isothermally, and then cooled to 20° C. at 20/min ramp. However, in the subsequent heating run it was observed the celecoxib is crystallized around 120° C. This indicates that the presence of sorbitol is also influencing the crystallization of celecoxib. Interestingly, in-situ generated dispersion showed two separate $T_g$s, corresponding to sorbitol and celecoxib. Presence of two separate $T_g$s, indicate the immiscibility of two components. DSC scans of in situ generated amorphous celecoxib and celecoxib:sorbitol physical mixture in 50:50% w/w is presented in FIG. 5.

Example 5: Celecoxib:Potassium Chloride 50:50% w/w

In-Situ Generated Amorphous Celecoxib

Accurately weighed amount of celecoxib was heated to 180° C. to melt crystalline celecoxib completely. It was held at 180° C. for 2 min isothermally, and then cooled to 20° C. at 20° C./min ramp. The in-situ generated amorphous celecoxib was subsequently heated at 20° C./min to determine the crystallization temperature. However, it was observed that, in-situ generated amorphous celecoxib did not crystallize in the subsequent heating Crystallization of Celecoxib in the Presence of Potassium Chloride Accurately weighed amount of celecoxib and potassium chloride physical mixture in 50:50% w/w was heated to 180° C. to melt crystalline celecoxib completely, and held at 180° C. for 2 min isothermally, and then cooled to 20° C. at 20/min ramp. However, in the subsequent heating run it was observed the celecoxib crystallized around 130° C. This indicates that the presence of potassium chloride is also influencing the crystallization of celecoxib. From this example, even presence of crystals of potassium chloride in the melt of celecoxib is also inducing crystallization because potassium chloride has a very high melting point of 770° C. DSC scans of in situ generated amorphous celecoxib and celecoxib:potassium chloride physical mixture in 50:50% w/w is presented in FIG. 6.

Example 6: Celecoxib:Urea 75:25% w/w

In-Situ Generated Amorphous Celecoxib

Accurately weighed amount of celecoxib was heated to 180° C. to melt crystalline celecoxib completely. It was held at 180° C. for 2 min isothermally, and then cooled to 20° C. at 20° C./min ramp. The in-situ generated amorphous celecoxib was subsequently heated at 20° C./min to determine the crystallization temperature. However, it was observed that, in-situ generated amorphous celecoxib did not crystallize in the subsequent heating Crystallization of Celecoxib in the Presence of Urea Accurately weighed amount of celecoxib and urea physical mixture in 75:25% w/w was heated to 180° C. to melt crystalline celecoxib completely, and held at 180° C. for 2 min isothermally, and then cooled to 20° C. at 20/min ramp. However, in the subsequent heating run it was observed the Tg of dispersion decreased to around 31.41° C. in the presence of urea in comparison to 59.57° C. of in-situ generated amorphous celecoxib. Decrease in Tg would also contribute to the crystallization tendency. This is well reported in literature related to amorphous state. This example indicated even excipients which decrease Tg of pharmaceutical active would have positive contribution on crystallization inducing capability. DSC scans of in-situ generated amorphous celecoxib and celecoxib:urea physical mixture in 75:25% w/w is presented in FIG. 7.

Example 7: Celecoxib:Mannitol 50:50 w/w (i) 2 gm of celecoxib was dissolved in 150 ml of methanol.
(ii) 2 gm of mannitol was dissolved in 50 ml of distilled water.
(iii) Aqueous mannitol was added to methanolic solution of celecoxib. The solution was spray dried using following parameters (Table 1).
(iv) DSC (FIG. 8) and MDSC indicated the crystalline nature of celecoxib in the dispersion.

TABLE 1

Spray drying parameters for preparation of celecoxib:mannitol 50:50 w/w dispersion

| Spray drying parameters | |
|---|---|
| Inlet temperature | 95° C. |
| Vacuum | −85 mm of WC |
| Feed rate | 3 ml/min |
| Atomization pressure | 1.4 Kg/sq. m |

TABLE 1-continued

Spray drying parameters for preparation of celecoxib:mannitol 50:50 w/w dispersion

| Spray drying parameters | |
|---|---|
| Outlet temperature | 35-40° C. |
| Mode of spray | Top spray |

Example 8: Celecoxib:Stearic Acid 50:50 w/w i. 2 gm of celecoxib and 2 gm of stearic acid were dissolved in 200 ml of methanol and spray dried using following parameters (Table 2).
ii. DSC (FIG. 9) and MDSC indicated the crystalline nature of celecoxib in the dispersion. The crystallite size measured from powder X-ray diffraction peak broadening (FIG. 10) by Scherrer equation was 395.10 nm.

TABLE 2

Spray drying parameters for preparation of celecoxib:stearic acid 50:50 w/w dispersion

| Spray drying parameters | |
|---|---|
| Inlet temperature | 140° C. |
| Vacuum | −110 mm of WC |
| Feed rate | 6 ml/min |
| Atomization pressure | 1.4 Kg/sq. m |
| Outlet temperature | 40-45° C. |
| Mode of spray | Top spray |

Example 9: Aceclofenac:Potassium Chloride 50:50 w/w i. 2 gm of aceclofenac was dissolved in 150 ml of methanol.
ii. 2 gm of potassium chloride was dissolved in 50 ml of distilled water.
iii. Aqueous potassium chloride solution was added to methanolic solution of aceclofenac. The solution was spray dried using following parameters (Table 3).
iv. DSC and MDSC indicated the crystalline nature of aceclofenac in the dispersion. The crystallite size measured from powder X-ray diffraction peak broadening (FIG. 11) by Scherrer equation was 294.60 nm.
v. The dissolution profiles (Table 4) of aceclofenac potassium chloride physical mixture and dispersion in 900 ml of Elga water at 100 rpm are presented in Table 19. 50 mg equivalent of aceclofenac in physical mixture and dispersion were taken for dissolution studies.

TABLE 3

Spray drying parameters for preparation of aceclofenac:potassium chloride dispersion 50:50 w/w

| Spray drying parameters | |
|---|---|
| Inlet temperature | 70° C. |
| Vacuum | −85 mm of WC |
| Feed rate | 6 ml/min |
| Atomization pressure | 1.4 Kg/sq. m |
| Outlet temperature | 18-23° C. |
| Mode of spray | Bottom spray |

TABLE 4

Dissolution profiles of aceclofenac:potassium
chloride physical mixture and aceclofenac:potassium
chloride dispersion in 50:50 w/w

| Time | % Release | |
|---|---|---|
| (min) | Physical Mixture | Dispersion |
| 0 | 0.00 | 0.00 |
| 5 | 6.54 | 42.60 |
| 10 | 9.17 | 57.16 |
| 20 | 15.23 | 67.27 |
| 30 | 18.21 | 71.20 |
| 40 | 21.81 | 73.38 |
| 50 | 27.01 | 73.82 |
| 60 | 26.64 | 73.84 |

Example 10: Nateglinide:Potassium Chloride 50:50 w/w i. 2 gm of nateglinide was dissolved in 150 ml of methanol.
ii. 2 gm of potassium chloride was dissolved in 50 ml of distilled water.
iii. Aqueous potassium chloride solution was added to methanolic solution of nateglinide. The solution was spray dried using following parameters (Table 5).
iv. DSC and MDSC indicated the crystalline nature of nateglinide in the dispersion. However, crystallite size of nateglinide in the dispersion could not be determined because nateglinide crystallized into mixture of polymorphs in the dispersion.
v. The dissolution profiles of nateglinide potassium chloride physical mixture and dispersion in 900 ml of Elga water at 100 rpm are presented in Table 6. 50 mg equivalent of nateglinide in physical mixture and dispersion were taken for dissolution studies.

TABLE 5

Spray drying parameters for preparation of
Nateglinide:potassium chloride dispersion 50:50 w/w

| Spray drying parameters | |
|---|---|
| Inlet temperature | 70° C. |
| Vacuum | −85 mm of WC |
| Feed rate | 6 ml/min |
| Atomization pressure | 1.4 Kg/sq. m |
| Outlet temperature | 18-23° C. |
| Mode of spray | Bottom spray |

TABLE 6

Dissolution profiles of nateglinide:potassium chloride
physical mixture and nateglinide potassium
chloride dispersion in 50:50 w/w

| Time | % Release | |
|---|---|---|
| (min) | Physical Mixture | Dispersion |
| 0 | 0.00 | 0.00 |
| 5 | 15.09 | 48.35 |
| 10 | 20.56 | 70.49 |
| 20 | 30.47 | 90.18 |
| 30 | 39.20 | 92.54 |
| 40 | 44.31 | 92.89 |
| 50 | 45.02 | 94.63 |
| 60 | 46.03 | 93.04 |

Example 11: Ibuprofen:Mannitol 50:50 w/w i. 2 gm of ibuprofen was dissolved in 150 ml of methanol
ii. 2 gm of mannitol was dissolved in 50 ml of distilled water.
iii. Aqueous mannitol solution was added to methanolic solution of ibuprofen. The solution was spray dried using following parameters (Table 7).
iv. DSC and MDSC indicated the crystalline nature of ibuprofen in the dispersion. The crystallite size measured from powder X-ray diffraction peak broadening (FIG. 12) by Scherrer equation was 502.70 nm.
v. The dissolution profiles of ibuprofen mannitol physical mixture and dispersion in 900 ml of Elga water at 100 rpm are presented in Table 8. 50 mg equivalent of ibuprofen in physical mixture and dispersion were taken for dissolution studies.

TABLE 7

Spray drying parameters for preparation of
ibuprofen:mannitol dispersion 50:50 w/w

| Spray drying parameters | |
|---|---|
| Inlet temperature | 70° C. |
| Vacuum | −85 mm of WC |
| Feed rate | 3 ml/min |
| Atomization pressure | 1.4 Kg/sq. m |
| Outlet temperature | 20-25° C. |
| Mode of spray | Bottom spray |

TABLE 8

Dissolution profiles of ibuprofen:mannitol physical
mixture and ibuprofen:mannitol dispersion in 50:50 w/w

| Time | % Release | |
|---|---|---|
| (min) | Physical Mixture | Dispersion |
| 0 | 0.00 | 0.00 |
| 5 | 15.30 | 63.32 |
| 10 | 21.09 | 68.55 |
| 20 | 28.99 | 71.36 |
| 30 | 33.58 | 76.31 |
| 40 | 40.08 | 84.43 |
| 50 | 39.78 | 82.62 |
| 60 | 44.47 | 84.94 |

Example 12: Aceclofenac:Stearic Acid 50:50 w/w i. 2 gm of aceclofenac and 2 gm of stearic acid were dissolved in 200 ml of methanol.
ii. The methanolic solution of aceclofenac and stearic acid is spray dried using following parameters (Table 9).
iii. DSC (FIG. 13) indicated the crystalline nature of aceclofenac in the dispersion.

TABLE 9

Spray drying parameters for preparation of
aceclofenac:stearic acid dispersion 50:50 w/w

| Spray drying parameters | |
|---|---|
| Inlet temperature | 70° C. |
| Vacuum | −85 mm of WC |
| Feed rate | 6 ml/min |
| Atomization pressure | 1.4 Kg/sq. m |
| Outlet temperature | 18-23° C. |
| Mode of spray | Top spray |

Example 13: Hesperetin:Mannitol 50:50 w/w i. 2 gm of hesperetin was dissolved in 150 ml of methanol
ii. 2 gm of mannitol was dissolved in 50 ml of distilled water.
iii. Aqueous mannitol solution was added to methanolic solution of hesperetin. The solution was spray dried using following parameters (Table 10).
iv. DSC and MDSC indicated the crystalline nature of hesperetin in the dispersion. The crystallite size measured from powder X-ray diffraction peak broadening (FIG. 14) by Scherrer equation was 141.06 nm.
v. The dissolution profiles of hesperetin powder and dispersion in 900 ml of 100 mM pH 6.8 phosphate buffer at 100 rpm are presented in Table 11. 60 mg equivalent of hesperetin as powder and dispersion were taken for dissolution studies.

TABLE 10

Spray drying parameters for preparation of hesperetin:mannitol dispersion 50:50 w/w

| Spray drying parameters | |
|---|---|
| Inlet temperature | 85° C. |
| Vacuum | −100 mm of WC |
| Feed rate | 3 ml/min |
| Atomization pressure | 1.2 Kg/sq. m |
| Outlet temperature | 20-25° C. |
| Mode of spray | Top spray |

TABLE 11

Dissolution profiles of hesperetin powder and hesperetin:mannitol dispersion in 50:50 w/w

| Time | % Release | |
|---|---|---|
| (min) | Hesperetin powder | Dispersion |
| 0 | 0.00 | 0.00 |
| 3 | 1.25 | 3.87 |
| 5 | 3.06 | 10.76 |
| 10 | 2.15 | 12.93 |
| 15 | 1.06 | 13.01 |
| 30 | 1.48 | 17.33 |
| 60 | 3.74 | 14.81 |
| 120 | 7.47 | 16.82 |

Example 14: Naringenin:Mannitol 50:50 w/w i. 2 gm of Naringenin was dissolved in 150 ml of methanol
ii. 2 gm of mannitol was dissolved in 50 ml of distilled water.
iii. Aqueous mannitol solution was added to methanolic solution of naringenin. The solution was spray dried using following parameters (Table 12).
iv. DSC and MDSC indicated the crystalline nature of naringenin in the dispersion. The crystallite size measured from powder X-ray diffraction peak broadening (FIG. 15) by Scherrer equation was 210.63 nm.
v. The dissolution profiles of naringenin powder and dispersion in 900 ml of 100 mM pH 6.8 phosphate buffer at 100 rpm are presented in Table 13. 60 mg equivalent of naringenin as powder and dispersion were taken for dissolution studies.

TABLE 12

Spray drying parameters for preparation of naringenin:mannitol dispersion 50:50 w/w

| Spray drying parameters | |
|---|---|
| Inlet temperature | 70° C. |
| Vacuum | −100 mm of WC |
| Feed rate | 3 ml/min |
| Atomization pressure | 1.2 Kg/sq. m |
| Outlet temperature | 20-25° C. |
| Mode of spray | Top spray |

TABLE 13

Dissolution profiles of naringenin:mannitol physical mixture and naringenin:mannitol dispersion in 50:50 w/w

| Time | % Release | |
|---|---|---|
| (min) | Naringenin powder | Dispersion |
| 0 | 1.60 | 3.88 |
| 3 | 5.84 | 10.69 |
| 5 | 9.54 | 17.11 |
| 10 | 11.52 | 17.69 |
| 15 | 17.32 | 23.09 |
| 30 | 23.34 | 25.87 |
| 60 | 26.25 | 34.81 |
| 120 | 25.14 | 34.58 |

Example 15: Indomethacin:Mannitol 50:50 w/w i. 2 gm of Indomethacin was dissolved in 200 ml of methanol.
ii. 2 gm of mannitol was dissolved in 50 ml of distilled water.
iii. Aqueous mannitol was added to methanolic solution of Indomethacin. The solution was spray dried using following parameters (Table 14).
iv. DSC (FIG. 16) and MDSC indicated the crystalline nature of Indomethacin in the dispersion. The crystallite size measured from powder X-ray diffraction peak broadening by Scherrer equation was 585.27 nm.

TABLE 14

Spray drying parameters for preparation of indomethacin:mannitol 50:50 w/w dispersion

| Spray drying parameters | |
|---|---|
| Inlet temperature | 60° C. |
| Vacuum | −100 mm of WC |
| Feed rate | 3 ml/min |
| Atomization pressure | 1.2 Kg/sq. m |
| Outlet temperature | 25-30° C. |
| Mode of spray | Down spray |

Example 16: Curcumin:Mannitol 66.67:33.33 w/w i. 600 mg of curcumin was dissolved in 40 ml of acetone.
ii. 300 mg of mannitol was dissolved in 12 ml of distilled water.
iii. Mannitol solution was added to solution of curcumin. The solution was spray dried using following parameters (Table 15).
vi. DSC and MDSC indicated the crystalline nature of curcumin in the dispersion. The crystallite size measured from powder X-ray diffraction peak broadening (FIG. 17) by Scherrer equation was 676.5 nm.

TABLE 15

Spray drying parameters for preparation of Curcumin:Mannitol 2:1 w/w dispersion

Spray drying parameters

| | |
|---|---|
| Inlet temperature | 145° C. |
| Vacuum | −95 mm of WC |
| Feed rate | 3 ml/min |
| Atomization pressure | 1.3 Kg/sq. m |
| Outlet temperature | 55-60° C. |
| Mode of spray | Bottom spray |

Example 17: Curcumin:Stearic Acid 50:50 w/w i. 2 gm of curcumin and 2 gm of stearic acid were dissolved in 200 ml of acetone.
ii. The solution was spray dried using following parameters (Table 1).
iii. DSC and MDSC indicated the crystalline nature of curcumin in the dispersion. The crystallite size measured from powder X-ray diffraction peak broadening by Scherrer equation was 398.6 nm.
iv. The dissolution profiles of curcumin powder and dispersion in fasted state simulated gastric fluid are presented in Table 2. Fasted state simulated gastric fluid contained sodium taurocholate (80 µM), lecithin (20 µM), pepsin (0.1 mg/ml), sodium chloride (34.2 mM), sodium lauryl sulphate (0.05% w/v) and hydrochloric acid (q.s. pH 1.6). Samples equivalent to 25 mg of CRM were added into 900 ml dissolution medium and incubated at 37±0.5° C. at 100 rpm.

TABLE 16

Spray drying parameters for preparation of Curcumin:Stearic acid 50:50 w/w dispersion Spray drying parameters

| | |
|---|---|
| Inlet temperature | 120° C. |
| Vacuum | −100 mm of WC |
| Feed rate | 3 ml/min |
| Atomization pressure | 1.3 Kg/sq. m |
| Outlet temperature | 55-60° C. |
| Mode of spray | Bottom spray |

TABLE 17

Dissolution profiles of curcumin:stearic acid physical mixture and curcumin:stearic acid dispersion 50:50 w/w

| Time | % Release | |
|---|---|---|
| (min) | Curcumin powder | Dispersion |
| 5 | 10.8 | 42.3 |
| 10 | 15.0 | 47.4 |
| 15 | 15.4 | 64.3 |
| 20 | 15.1 | 66.5 |
| 30 | 15.1 | 74.1 |
| 40 | 15.2 | 81.8 |
| 60 | 15.0 | 82.0 |
| 80 | 15.2 | 83.4 |
| 100 | 15.6 | 82.8 |
| 120 | 15.3 | 83.6 |

Example 18: Accelerated Stability Studies (40° C./75% RH) of Celecoxib:Stearic acid 50:50 w/w i. Nanocrystalline solid dispersion of celecoxib:stearic acid 50:50 w/w, prepared as described in example 8, was subjected to accelerated stability studies at 40° C./75% RH.
ii. To determine the crystallite size during the stability studies peak broadening of PXRD peaks characteristic to Celecoxib were monitored.
iii. Crystallite size, determined by Scherrer equation, of Celecoxib in nanocrystalline solid dispersion during stability studies period is tabulated in Table 16. Overlay of PXRD scans of stability samples of Celecoxib Stearic acid nanocrystalline solid dispersions is presented in FIG. 18.

TABLE 18

Crystallite size of Celecoxib in nanocrystalline solid dispersion during stability studies

| | Crystallite Size (in nm) at time point | | | |
|---|---|---|---|---|
| Dispersion | 0 days | 15 days | 30 days | 60 days |
| Celecoxib:mannitol 50:50 w/w | 400.09 | 436.55 | 421.95 | 417.95 |

Example 19: Accelerated Stability Studies (40° C./75% RH) of Aceclofenac:Potassium Chloride 50:50 w/w i. Nanocrystalline solid dispersion of aceclofenac:potassium chloride 50:50 w/w, prepared as described in example 10, was subjected to accelerated stability studies at 40° C./75% RH.
ii. To determine the crystallite size during the stability studies peak broadening of PXRD peaks characteristic to Aceclofenac were monitored.
iii. Crystallite size, determined by Scherrer equation, of Aceclofenac in nanocrystalline solid dispersion during stability studies period is tabulated in Table 17. Overlay of PXRD scans of stability samples of Aceclofenac Potassium Chloride nanocrystalline solid dispersions is presented in FIG. 19.
iv. Dissolution of aceclofenac:potassium chloride dispersion subjected to accelerated stability conditions (40° C./75% RH) for 2 months was performed in 900 ml of Elga water at 100 rpm. % release of stability sample and initial sample are presented in Table 18. 50 mg equivalent of Aceclofenac in dispersion was taken for dissolution studies.

TABLE 19

Crystallite size of Aceclofenac in nanocrystalline solid dispersion during stability studies

| | Crystallite Size (in nm) at time point | | | |
|---|---|---|---|---|
| Dispersion | 0 days | 15 days | 30 days | 60 days |
| Aceclofena:potassium chloride 50:50 w/w | 395.10 | 417.16 | 426.39 | 421.82 |

TABLE 20

Dissolution profiles of aceclofenac:potassium chloride physical mixture and aceclofenac:Potassium chloride dispersion in 50:50 w/w

| Time | % Release of accelerated stability samples | | |
|---|---|---|---|
| (min) | 0 days | 60 days | 120 days |
| 0 | 0.00 | 0.00 | 0.00 |
| 5 | 42.60 | 41.57 | 38.74 |
| 10 | 57.16 | 54.71 | 53.31 |
| 20 | 67.27 | 68.46 | 68.46 |
| 30 | 71.20 | 69.62 | 67.61 |
| 40 | 73.38 | 74.31 | 73.81 |
| 50 | 73.82 | 77.50 | 74.34 |
| 60 | 73.84 | 75.21 | 71.65 |
| 30 | 76.31 | 75.21 | 77.74 |
| 40 | 84.43 | 80.28 | 82.24 |
| 50 | 82.62 | 81.07 | 82.22 |
| 60 | 84.94 | 80.74 | 81.22 |

Example 20: Accelerated Stability Studies (40° C./75% RH) of Nateglinide:Potassium Chloride 50:50 w/w i. Nanocrystalline solid dispersion of Nateglinide:Potassium chloride 50:50 w/w, prepared as described in example 10, was subjected to accelerated stability studies at 40° C./75% RH.
ii. To determine the crystallite size during the stability studies peak broadening of PXRD peaks characteristic to Nateglinide was monitored.
iii. Dissolution of Nateglinide potassium chloride dispersion subjected to accelerated stability conditions (40° C./75% RH) for 2 months was performed in 900 ml of Elga water at 100 rpm. % release of stability sample and initial sample are presented in Table 19. 50 mg equivalent of Nateglinide in dispersion was taken for dissolution studies.

TABLE 21

Dissolution profiles of Nateglinide:Potassium chloride physical mixture and Nateglinide:potassium chloride dispersion in 50:50 w/w

| Time | % Release of accelerated stability samples | | |
|---|---|---|---|
| (min) | 0 days | 60 days | 120 days |
| 0 | 0.00 | 0.00 | 0.00 |
| 5 | 48.35 | 41.77 | 41.35 |
| 10 | 70.49 | 81.12 | 81.31 |
| 20 | 90.18 | 86.73 | 83.74 |
| 30 | 92.54 | 89.91 | 86.01 |
| 40 | 92.89 | 92.65 | 84.62 |
| 50 | 94.63 | 89.16 | 90.75 |
| 60 | 93.04 | 89.51 | 88.42 |

Example 21: Accelerated Stability Studies (40° C./75% RH) of Ibuprofen:Mannitol 50:50 w/w i. Nanocrystalline solid dispersion of Ibuprofen:Mannitol 50:50 w/w was prepared as described in example 11 and was subjected to accelerated stability studies at 40° C./75% RH.
ii. To determine the crystallite size during the stability studies peak broadening of PXRD peaks characteristic to Ibuprofen were monitored.
iii. Crystallite size, determined by Scherrer equation, of Ibuprofen in nanocrystalline solid dispersion during stability studies period is tabulated in Table 20. Overlay of PXRD scans of stability samples of Ibuprofen:Mannitol nanocrystalline solid dispersions are presented in FIG. 20.
iv. Dissolution of Ibuprofen:mannitol dispersion subjected to accelerated stability conditions (40° C./75% RH) for 2 months was performed in 900 ml of Elga water at 100 rpm. % release of stability sample and initial sample are presented in Table 21. 50 mg equivalent of Aceclofenac in dispersion was taken for dissolution studies.

TABLE 22

Crystallite size of Ibuprofen in nanocrystalline solid dispersion during stability studies

| Dispersion | Crystallite Size (in nm) at time point | | | |
|---|---|---|---|---|
| | 0 days | 15 days | 30 days | 60 days |
| Ibuprofen:mannitol 50:50 w/w | 502.70 | 585.12 | 606.67 | 589.87 |

TABLE 23

Dissolution profiles of Ibuprofen and Mannitol physical mixture and Ibuprofen:Mannitol dispersion in 50:50 w/w

| Time | % Release of accelerated stability samples | | |
|---|---|---|---|
| (min) | 0 days | 60 days | 120 days |
| 0 | 0.00 | 0.00 | 0.00 |
| 5 | 63.32 | 57.45 | 59.31 |
| 10 | 68.55 | 70.81 | 70.07 |
| 20 | 71.36 | 71.01 | 72.36 |

Example 22: Oral Bioavailability Studies

Hesperetin:Mannitol Dispersion 50:50 w/w Oral Bioavailability Study

Hesperetin:Mannitol physical mixture 50:50 w/w (HRN-M-PM) showed a $C_{max}$ of 297.3 ng/ml, 0.6 h post dosing and a $t_{1/2}$ of 0.14 h. The mean $AUC_{0-\infty}$ was found to be 2074.9 ng·h/ml for HRN-M-PM. On the other hand, hesperetin:mannitol nanocrystalline solid dispersion 50:50 w/w (HRN-M) showed improvement in the $C_{max}$ to 534.4 ng/ml, average $T_{max}$ was observed to be 0.8 h and $AUC_{0-\infty}$ of 4680.1 ng·h/ml. $C_{max}$ showed statistically significant improvement of 1.79-folds, over the control. The oral bioavailability ($AUC_{0-\infty}$) improvement of 2.86-folds was also statistically significant. Table 3 enlists the pharmacokinetic parameters for HRN-M and HRN-M-PM. This study proved the efficacy and superiority of nanocrystalline solid dispersion over crude physical mixture in terms of bioavailability advantage.

TABLE 24

Pharmacokinetic parameters of hesperetin observed after administration of HRN-M and HRN-M-PM after single oral dose (80 mg kg$^{-1}$) to male SD rats (n = 5)

| Formulation | Pharmacokinetic parameters | | | |
|---|---|---|---|---|
| | $C_{max}$ (ng/ml) | $T_{max}$ (h) | $t_{1/2}$ (h) | $AUC_{0-\infty}$ (ng · h/ml) |
| HRN-M-PM | 297.3 ± 98.91 | 0.6 ± 0.22 | 0.14 ± 0.05 | 1129.1 ± 643.56 |
| HRN-M | *534.4 ± 115.24 | 0.8 ± 0.27 | 0.05 ± 0.021 | *3236.5 ± 858.99 |

*P < 0.05, statistically significant difference in comparison with HRN-M-PM

Curcumin:Stearic Acid Dispersion 50:50 w/w Oral Bioavailability Study

The mean plasma concentration-time profiles after oral administration of spray dried curcumin (control) and curcumin:stearic acid nanocrystalline solid dispersion 50:50 w/w (CRM-SA) are shown in FIG. 2 and pharmacokinetic parameters are shown in Table 4. Control provided $C_{max}$ and $AUC_{0-\infty}$ of 58.1 ng/ml and 76.2 ng·h/ml respectively. On the other hand, CRM-SA provided $C_{max}$ and $AUC_{0-\infty}$ of 245.9 ng/ml and 1156.3 ng·h/ml respectively. The oral bioavailability ($AUC_{0-\infty}$) improvement of 15.17-folds was also statistically significant. Biological half life ($t_{1/2}$) of CRM was improved by CRM-SA and curcumin was present in detectable concentration range even 24 h after administration. Compared to control, CRM-SA provided statistically significant improvement in all of the studied pharmacokinetic parameters.

TABLE 25

Pharmacokinetic parameters of curcumin observed after administration of control and CRM-SA after single oral dose (250 mg kg$^{-1}$) to female SD rats (n = 5)

| Sample | Pharmacokinetic parameters | | | |
|---|---|---|---|---|
| | $C_{max}$ (ng/ml) | $T_{max}$ (h) | $t_{1/2}$ (h) | $AUC_{0-\infty}$ (ng · h/ml) |
| Control | 58.1 ± 7.3 | 0.6 ± 0.1 | 1.4 ± 0.3 | 76.2 ± 6.2 |
| CRM-SA | *245.9 ± 23.3 | *1.1 ± 0.2 | 13.5 ± 1.3* | *1156.3 ± 24.9 |

*P < 0.05, statistically significant difference in comparison with control

Celecoxib:Mannitol Dispersion 50:50 w/w Oral Bioavailability Study

Celecoxib:mannitol physical mixture 50:50 w/w (CLB-M-PM) showed a $C_{max}$ of 321.1 ng/ml, 8 h post dosing. The mean $AUC_{0-\infty}$ was found to be 3242.3 ng·h/ml for (CLB-M-PM). On the other hand, celecoxib:mannitol nanocrystalline solid dispersion 50:50 w/w (CLB-M) showed improvement in the $C_{max}$ to 513.4 ng/ml, average $T_{max}$ was observed to be 4 h and $AUC_{0-\infty}$ of 5295.8 ng·h/ml. $C_{max}$ showed statistically significant improvement of 1.6-folds, over the control. The oral bioavailability ($AUC_{0-\infty}$) improvement of 1.63-folds was also statistically significant. Table 5 enlists the pharmacokinetic parameters for CLB-M and CLB-M-PM. This study proved the efficacy and superiority of nanocrystalline solid dispersion over crude physical mixture in terms of bioavailability advantage.

TABLE 26

Pharmacokinetic parameters of celecoxib observed after administration of CLB-M and CLB-M-PM after single oral dose (5 mg kg$^{-1}$) to female SD rats (n = 5)

| Formulation | Pharmacokinetic parameters | | |
|---|---|---|---|
| | $C_{max}$ (ng/ml) | $T_{max}$ (h) | $AUC_{0-\infty}$ (ng · h/ml) |
| CLB-M-PM | 321.1 ± 53.44 | 8 ± 2.88 | 3242.3 ± 266.19 |
| CLB-M | *513.4 ± 200.74 | 4 ± 2.5 | 5295.8 ± 2747.30 |

* P < 0.05, statistically significant difference in comparison with CLB-M-PM

ADVANTAGES OF THE PRESENT INVENTION

1. The present invention provides a one step process to obtain composition containing nanocrystalline solid dispersion.
2. The one step process of the present invention can be applied to a wide range of pharmaceutical actives to enhance dissolution.
3. The process of the present invention is applicable to both hydrophobic and hydrophilic pharmaceutical active.
4. Composition prepared from the process of the present invention is stable.
5. Composition of the present invention is in powder form comprising discrete particles, with enhanced solubility and dispersibility.
6. Composition of the present invention is useful for pharmaceutical, veterinary and neutraceutical applications.

The invention claimed is:

1. A method for preparing discrete particles of a nanocrystalline solid dispersion comprising:
   a) dissolving at least one active ingredient in at least one first solvent to produce solution A;
   b) dissolving at least one crystallization inducer excipient in at least one second solvent to produce solution B;
   c) mixing of said solution A and solution B in a proportion to produce solution C;
   d) drying of solution C to evaporate the first and second solvents and to form the said discrete particles of said nanocrystalline solid dispersion, wherein the solvent evaporation and formation of discrete particles from Solution C is carried out by spray drying, vacuum drying, or solvent evaporation, and wherein drying is carried out at a temperature above the glass transition temperature of active ingredient or the glass transition temperature of active ingredient in combination with crystallization inducer(s) optionally along with pharmaceutically acceptable excipient(s) and below the melting point of the active ingredient in presence of crystallization inducer(s) optionally along with pharmaceutically acceptable excipient(s);
   wherein said discrete particles of nanocrystalline solid dispersion are in powder form;
   wherein said discrete particle comprises crystals of said active ingredient(s) in a matrix of the said crystallization inducer(s) and/or coexisting with crystals of crystallization inducer(s), optionally along with pharmaceutically acceptable excipient(s) which further may be soluble completely or partially.

2. The method according to claim 1, wherein said discrete particles of nanocrystalline solid dispersion comprises crystals of at least one active ingredient;
   wherein the active ingredient is pharmaceutical active or veterinary active or nutraceutical active; dispersed in the matrix of at least one crystallization inducer and/or coexisting with crystals of crystallization inducer, optionally along with pharmaceutically acceptable excipients.

3. The method according to claim 1, wherein said discrete particles of nanocrystalline solid dispersion comprises crystals of at least one active ingredient present in the range of 0.01% to 95% of said powder form, and the crystallization inducer is present in the range of 99.99% to 5% of said powder form.

4. The method according to claim 1, wherein said discrete particles of nanocrystalline solid dispersion comprises the crystals of active ingredient; wherein the said crystals of active ingredient comprises in the size range of 10 nm to 1000 nm.

5. The method according to claim 1, wherein at least about 90% of said discrete particles lie in the range of 0.5 to 20 micron.

6. The method according to claim 1, wherein said active ingredient comprises one or more of acetylcholinesterase inhibitors, analgesics and nonsteroidal anti-inflammatory agents (NSAIDs), antihelminthics, antiacne agents, antianginal agents, antiarrhythmic agents, anti-asthma agents, antibacterial agents, anti-benign prostate hypertrophy (BPH) agents, anticancer agents and immunosuppressants, anticoagulants, antidepressants, antidiabetics, antiepileptics, antifungal agents, antigout agents, antihypertensive agents, antimalarial agents, antimigraine agents, antimuscarinic agents, antiparkinsonian agents, antiprotozoal agents, antithyroid agents, antitussive agent, antiviral agents, anxiolytics, sedatives, hypnotics and neuroleptics, beta-blockers, cardiac inotropic agents, corticosteroids, diuretics, gastrointestinal agents, histamine $H_1$- and $H_2$-receptor antagonists, keratolytic agents, lipid regulating/hypolipidemic agents, muscle relaxants, opioid analgesics, sex hormones and stimulants.

7. The method according to claim 1, wherein said active ingredient selected alone or in combination of celecoxib, aceclofenac, nateglinide, ibuprofen, hesperetin, naringenin, resveratrol, curcumin, albendazole fenbendazole, itraconazole, calcitriol, carotenes, chrysin, dihydrotachysterol, flavonoids, jasmonates, lipoic acid, lutein, lycopene, phytonadiol, quercetin, vitamins including vitamin A, vitamin $B_2$, vitamin D and derivatives, vitamin E, and vitamin K, coenzyme Q10 (ubiquinone), essential fatty acids, nonessential fatty acids, plant extracts and minerals.

8. The method according to claim 1, wherein said crystallization inducer comprises one or more of sugars, sugar alcohols, acids, bases, inorganic salts, amino acids, surfactants, carbohydrates, phospholipids, lipids, proteins, preservatives, salts and hydrates thereof.

9. The method according to claim 1, wherein said crystallization inducer comprises one or more from the group of mannitol, stearic acid, cetosteary alcohol, sorbitol, potassium chloride, and urea, and salts and hydrates thereof.

10. The method according to claim 1, wherein said active ingredient selected alone or in combination of a non-steroidal anti-inflammatory drug (NSAID) or anti-diabetic drug selected from celecoxib, nateglinide, aceclofenac, ibuprofen, hesperetin, naringenin and curcumin; and crystallization-inducer is a polyol or a saturated fatty acid or an inorganic salt selected from mannitol, sorbitol, stearic acid and potassium chloride.

11. The method according to claim 1, wherein said discrete particles of the nanocrystalline solid dispersion are further used to formulate dosage forms suitable for oral administration.

12. The method according to claim 1, wherein said discrete particles of nanocrystalline solid dispersion are stable against crystal growth of active ingredient within shelf-life and does not exhibit any changes in the chemical or physicochemical properties.

13. The method according to claim 1, wherein pharmaceutically acceptable excipients comprises one or more of solubilizers, pH modifying agents, aggregation inhibitors, buffers, surfactants, desiccating agents, surface stabilizers, antiadherents, lubricants, glidants, binders, coating agents, disintegrants, diluents, flavoring agents, coloring agents, preservatives and sweeteners.

14. The method according to claim 1, wherein the drying of Solution C is carried out by Spray drying.

15. The method according to claim 1, wherein either the first or second solvent comprises one or more of polar solvents, nonpolar solvents, polar aprotic solvents and polar protic solvents.

16. The method according to claim 1, wherein either the first or second solvent comprises one or more of acetic acid, acetonitrile, acetone, 1-butanol, 2-butanol, N,N-dimethylacetamide; N,N-dimethylformamide, dimethyl sulfoxide, 1,4-dioxane, ethanol, formic acid, methanol, 3-methyl-1-butanol, methylethyl ketone, 2-methyl-1-propanol, 1-methyl-2-pyrrolidone, 1-pentanol, 1-propanol, 2-propanol, tetrahydrofuran, ethanol, water and mixtures thereof.

17. The method according to claim 1, wherein the first and second solvents are the same.

18. The method according to claim 12, wherein said discrete particles of nanocrystalline solid dispersion exhibit enhanced dissolution rate.

* * * * *